US009504551B2

(12) United States Patent
Shrivastava et al.

(10) Patent No.: US 9,504,551 B2
(45) Date of Patent: Nov. 29, 2016

(54) APPARATUS FOR FILTERING A BODY LUMEN

(75) Inventors: Sanjay Shrivastava, Irvine, CA (US); Milisav Obradovic, Lörrach (DE); Nie Tang, San Jose, CA (US); Rainer Bregulla, Ballingen (DE); Michael L. Green, Pleasanton, CA (US)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 1130 days.

(21) Appl. No.: 13/140,369

(22) PCT Filed: Dec. 16, 2009

(86) PCT No.: PCT/US2009/068301
§ 371 (c)(1),
(2), (4) Date: Dec. 12, 2011

(87) PCT Pub. No.: WO2010/077973
PCT Pub. Date: Jul. 8, 2010

(65) Prior Publication Data
US 2012/0083823 A1 Apr. 5, 2012

Related U.S. Application Data

(60) Provisional application No. 61/138,458, filed on Dec. 17, 2008, provisional application No. 61/138,466, filed on Dec. 17, 2008, provisional application No. 61/138,485, filed on Dec. 17, 2008, provisional application No. 61/138,509, filed on Dec. 17, 2008.

(51) Int. Cl.
*A61M 29/00* (2006.01)
*A61F 2/01* (2006.01)
*A61F 2/848* (2013.01)

(52) U.S. Cl.
CPC ............ *A61F 2/01* (2013.01); *A61F 2002/011* (2013.01); *A61F 2002/016* (2013.01); *A61F 2002/8486* (2013.01); *A61F 2230/0006* (2013.01); *A61F 2230/008* (2013.01); *A61F 2250/0067* (2013.01)

(58) Field of Classification Search
CPC .............. A61F 2/01; A61F 2002/011; A61F 2230/008; A61F 2230/0006; A61F 2002/8486; A61F 2002/016; A61F 2250/0067; A61F 2/013; A61F 2/018; A61F 2/848; A61F 2002/8483
See application file for complete search history.

(56) References Cited

U.S. PATENT DOCUMENTS 6,013,093 A * 1/2000 Nott et al. ................... 606/200
6,142,987 A 11/2000 Tsugita
(Continued)

FOREIGN PATENT DOCUMENTS

EP 0462008 12/1991
EP 1138277 10/2001
(Continued)

OTHER PUBLICATIONS

"Apex", Merriam-Webster.com, Merriam—Webster, n.d. Accessed Dec. 2, 2013, http://merriam-webster.com/dectionary/apex.
(Continued)

*Primary Examiner* — Gregory Anderson
*Assistant Examiner* — Son Dang
(74) *Attorney, Agent, or Firm* — Workman Nydegger; John Kwok

(57) ABSTRACT

An implantable lumen filter (200) is described. The implantable lumen filter includes a body (202) having a proximal end (202a), a distal end (202b), and a generally tapered outer surface (204). The outer surface is formed by a plurality of struts (206a, 206b). The plurality of struts forms a plurality of apertures (210). The apertures are dimensioned to inhibit and/or to lyse particulates of a selected size from passing through the apertures. The body (202) is transitionable from a collapsed state toward a deployed state. The implantable lumen filter includes an engaging portion (220) having a proximal end (220a) and a distal end (220b). The proximal end of the engaging portion is connected to a distal end of the body. The engaging portion has a generally annular shape and is configured to engage an inner surface of a body lumen.

20 Claims, 21 Drawing Sheets

(56) References Cited

U.S. PATENT DOCUMENTS

| | | |
|---|---|---|
| 6,171,328 B1 | 1/2001 | Addis |
| 6,214,025 B1 * | 4/2001 | Thistle et al. ............... 606/200 |
| 6,245,012 B1 * | 6/2001 | Kleshinski ................. 623/1.11 |
| 6,267,777 B1 | 7/2001 | Bosma et al. |
| 6,443,972 B1 | 9/2002 | Bosma et al. |
| 6,468,291 B2 | 10/2002 | Bates et al. |
| 6,517,559 B1 | 2/2003 | O'Connell |
| 6,517,573 B1 * | 2/2003 | Pollock .................... A61F 2/07 623/1.13 |
| 6,540,722 B1 | 4/2003 | Boyle et al. |
| 6,702,834 B1 | 3/2004 | Boylan et al. |
| 6,939,361 B1 * | 9/2005 | Kleshinski ................. 606/200 |
| 2001/0025187 A1 | 9/2001 | Okada |
| 2003/0149475 A1 | 8/2003 | Hyodoh et al. |
| 2003/0208224 A1 | 11/2003 | Broome |
| 2003/0208227 A1 | 11/2003 | Thomas |
| 2005/0004596 A1 | 1/2005 | McGuckin, Jr. et al. |
| 2005/0131452 A1 | 6/2005 | Walak et al. |
| 2006/0025852 A1 | 2/2006 | Armstrong et al. |
| 2006/0058836 A1 | 3/2006 | Bose et al. |
| 2006/0122686 A1 * | 6/2006 | Gilad et al. ................. 623/1.13 |
| 2006/0287717 A1 * | 12/2006 | Rowe .................... A61F 2/2412 623/2.11 |
| 2008/0097518 A1 * | 4/2008 | Thinnes et al. ............... 606/200 |
| 2010/0211161 A1 * | 8/2010 | Dreher .................... A61F 2/91 623/1.16 |
| 2012/0071914 A1 | 3/2012 | Shrivastava |

FOREIGN PATENT DOCUMENTS

| | | |
|---|---|---|
| EP | 1557137 | 7/2005 |
| WO | WO 00/56390 | 9/2000 |
| WO | WO 2007/067451 | 6/2007 |
| WO | WO 2008/066881 | 6/2008 |
| WO | WO 2010/077963 | 7/2010 |
| WO | WO 2010/077973 | 7/2010 |

OTHER PUBLICATIONS

U.S. Appl. No. 13/131,255, Nov. 27, 2013, Office Action.
U.S. Appl. No. 61/138,458, filed Dec. 17, 2008, Shrivastava et al.
U.S. Appl. No. 61/138,466, filed Dec. 17, 2008, Shrivastava et al.
U.S. Appl. No. 61/138,470, filed Dec. 17, 2008, Shrivastava.
U.S. Appl. No. 61/138,485, filed Dec. 17, 2008, Obradovic.
U.S. Appl. No. 61/138,509, filed Dec. 17, 2008, Shrivastava et al.
U.S. Appl. No. 13/131,255, Jul. 31, 2013, Office Action.
U.S. Appl. No. 13/131,255, Nov. 3, 2014, Office Action.
U.S. Appl. No. 13/131,255, Mar. 11, 2015, Notice of Allowance.

* cited by examiner

APPARATUS FOR FILTERING A BODY LUMEN

CROSS-REFERENCE TO RELATED APPLICATIONS

This patent application is a U.S. National Stage of International Application No. PCT/US2009/068301, filed on Dec. 16, 2009, which claims the benefit of and priority to U.S. Provisional Patent Application having Ser. No. 61/138,458, filed on Dec. 17, 2008, U.S. Provisional Patent Application having Ser. No. 61/138,509, filed on Dec. 17, 2008, U.S. Provisional Patent Application having Ser. No. 61/138,466, filed on Dec. 17, 2008, and U.S. Provisional Patent Application having Ser. No. 61/138,485, filed on Dec. 17, 2008, the disclosures of which are incorporated herein by reference in their entireties.

FIELD OF THE INVENTION

The present invention relates generally to medical devices, and more particularly to methods and apparatuses for filtering a body lumen.

BACKGROUND OF THE INVENTION

Vein thrombosis is a medical condition wherein a blood clot, or thrombus, has formed inside a vein. Such a clot often develops in the calves, legs, or lower abdomen, but can also affect other veins in the body. The clot may partially or completely block blood flow, and may break off and travel through the bloodstream. Commonly, the clot is caused by a pooling of blood in the vein, often when an individual is bed-ridden for an abnormally long duration of time, for example, when resting following surgery or suffering from a debilitating illness, such as a heart attack or traumatic injury. However, there are many other situations that cause the formation of a blood clot.

Vein thrombosis is a serious problem because of the danger that the clot may break off and travel through the bloodstream to the lungs, causing a pulmonary embolism. This is similar to a blockage of the blood supply to the lungs that causes severe hypoxia and cardiac failure, and frequently results in death. For many patients, anti-coagulant drug therapies may be sufficient to dissipate the clots. For example, patients may be treated with anticoagulants such as heparin and with thrombolytic agents such as streptokinase.

Unfortunately, some patients may not respond to such drug therapy or may not tolerate such therapy. Also, there may be other reasons why an anticoagulant is not desirable. For example, patients may have an acute sensitivity to heparin or may suffer from prolonged internal and/or external bleeding as a result of such drug therapies. Also, such drug therapies simply may be ineffective in preventing recurrent pulmonary emboli. In such circumstances, surgical procedures are required to prevent pulmonary emboli. One current standard of therapy for prevention of pulmonary emboli in patients who are classified high-risk or are unable to be anticoagulated is percutaneous insertion and placement of an inferior vena cava filter device.

Vena cava filters are devices which are implanted, usually in the inferior vena cava, providing a mechanical barrier to undesirable particulates. The filters may be used to filter peripheral venous blood clots and other particulates, which if remaining in the blood stream can migrate in the pulmonary artery or one of its branches and cause harm. Filters may also be implanted prophylactically in pregnant women and/or morbidly obese patients going through a surgery to prevent thrombi or emboli from reaching the lungs and causing pulmonary embolism.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one embodiment, an implantable lumen filter is described. The implantable lumen filter includes a body having a proximal end, a distal end, and a generally tapered outer surface. The outer surface is formed by a plurality of struts. The plurality of struts forms a plurality of apertures. The apertures are dimensioned to inhibit and/or to lyse particulates of a selected size from passing through the apertures and being dimensioned to allow blood components smaller than the selected size to pass through the apertures. The body is transitionable from a collapsed state toward a deployed state. The distal end has a first outer dimension. The implantable lumen filter includes an engaging portion having a proximal end and a distal end. The proximal end has a first outer dimension. The proximal end is operatively connected to a distal end of the body. The engaging portion has a generally annular shape. The engaging portion is configured to engage an inner surface of a body lumen.

In some embodiments, at least a portion of said plurality of struts may form a plurality of generally diamond shaped apertures. The engaging portion may include a plurality of struts with a plurality of struts extending generally parallel to a longitudinal axis and a plurality of struts connecting at least two longitudinally extending struts. The proximal end of the engaging portion may be connected to the distal end of the body by connecting at least one longitudinally extending strut of the engaging portion with at least one strut of the body. The plurality of struts may have a plurality of struts connecting at least two longitudinally extending struts.

The plurality of struts, in other embodiments, may have a plurality of struts extending generally parallel to a longitudinal axis. The engaging portion may include a plurality of struts, at least a portion of which form a plurality of generally diamond shaped apertures. The proximal end of the engaging portion may be connected to the distal end of the body by connecting at least one strut of the engaging portion near an apex of one of the generally diamond shaped apertures of the engaging portion with at least one longitudinally extending strut of the body.

In some embodiments, the engaging portion may include a distal portion of the apertures that may be generally aligned about a longitudinal axis of the engaging portion. In further embodiments, the engaging portion may include a proximal portion of the apertures that may be aligned about the longitudinal axis of the engaging portion. In still further embodiments, the engaging portion may include at least one intermediate portion of the apertures that may be generally aligned about the longitudinal axis of the engaging portion.

In some embodiments, the first outer dimension of the body may be about the same size as the first outer dimension of the engaging portion. In further embodiments, the body may have a first longitudinal dimension generally parallel with a longitudinal axis of the body and the engaging portion may have a first longitudinal dimension generally parallel with a longitudinal axis of the engaging portion such that the first longitudinal dimension of the body may be about two-thirds larger than the first longitudinal dimension of the engaging portion.

At least a portion of the engaging portion and the struts of the body may include cobalt chromium and/or alloys thereof or Nitinol and/or alloys thereof. At least a portion of the engaging portion and the body may be coated with a thrombo-resistant, anti-proliferative, and/or anti-inflammatory coating. At least a portion of the material of the engaging portion and the body may have a thrombo-resistant, anti-proliferative, and/or anti-inflammatory component incorporated therein.

In another embodiment, an implantable lumen filter is described. The implantable lumen filter includes a body having a proximal end, a distal end, and a plurality of struts. The body has a generally tapered shape. At least a portion of the plurality of struts form a plurality of generally diamond shaped apertures. The apertures are dimensioned to inhibit and/or lyse particulates of a selected size from passing through the apertures and are dimensioned to allow blood components smaller than the selected size to pass through the apertures. The body is transitionable from a collapsed state toward a deployed state. The distal end has a first outer dimension. The implantable lumen filter includes an engaging portion having a proximal end, a distal end, a generally annular shape, and a plurality of struts. At least a portion of the plurality of struts of the engaging portion form a plurality of generally diamond shaped apertures. The proximal end of the engaging portion has a first outer dimension. The proximal end of the engaging portion is connected to the distal end of the body by connecting at least one strut of the engaging portion near an apex of one of the generally diamond shaped apertures of the engaging portion with at least one strut of the body near an apex of one of the generally diamond shaped apertures of the body. The engaging portion is configured to engage an inner surface of a body lumen.

The implantable lumen filter, in some embodiments, includes a proximal portion of the apertures of the engaging portion. The proximal portion may be generally aligned about a longitudinal axis of the engaging portion. The implantable lumen filter, in further embodiments, includes a distal portion of the apertures of the engaging portion. The distal portion may be generally aligned about a longitudinal axis of the engaging portion. The implantable lumen filter, in still further embodiments, includes at least one intermediate portion of the apertures of the engaging portion. The at least one intermediate portion may be generally aligned about a longitudinal axis of the engaging portion.

In some embodiments, at least a portion of the plurality of struts of the engaging portion form a plurality of generally diamond shaped apertures in the proximal portion and the distal portion of the engaging portion. A proximal end of the proximal portion may be connected to the distal end of the body by connecting at least one strut of the proximal portion near an apex of one of the generally diamond shaped apertures of the proximal portion with at least one strut of the body near an apex of one of the generally diamond shaped apertures of the body. A proximal end of the distal portion may be connected to a distal end of the proximal portion by connecting at least one strut near a distal end of the proximal portion near an apex of one of the generally diamond shaped apertures of the proximal portion with at least one strut near a proximal end of the distal portion near an apex of one of the generally diamond shaped apertures of the distal portion.

In a further embodiment, an implantable lumen filter is described. The implantable lumen filter includes a body having a proximal end, a distal end, and a plurality of struts. The body has a generally tapered shape. The plurality of struts have a plurality of struts extending generally parallel to a longitudinal axis of the body and a plurality of struts connecting at least two longitudinally extending struts. The plurality of struts form a plurality of apertures. The apertures are dimensioned to inhibit and/or lyse particulates of a selected size from passing through the apertures and are dimensioned to allow blood components smaller than the selected size to pass through the apertures. The body is transitionable from a collapsed state toward a deployed state. The distal end has a first outer dimension. The implantable lumen filter includes an engaging portion having a proximal end, a distal end, a generally annular shape, and a plurality of struts having a plurality of struts extending generally parallel to a longitudinal axis of the engaging portion and a plurality of struts connecting at least two longitudinally extending struts. The proximal end has a first outer dimension. The proximal end of the engaging portion is connected to the distal end of the body by connecting at least one longitudinally extending strut of the engaging portion with at least one longitudinally extending strut of the body. The engaging portion is configured to engage an inner surface of a body lumen.

The implantable lumen filter, in some embodiments, includes a proximal portion of the apertures of the engaging portion. The proximal portion may be generally aligned about a longitudinal axis of the engaging portion. The implantable lumen filter, in further embodiments, includes a distal portion of the apertures of the engaging portion. The distal portion may be generally aligned about a longitudinal axis of the engaging portion. The implantable lumen filter, in still further embodiments, includes at least one intermediate portion of the apertures of the engaging portion. The at least one intermediate portion may be generally aligned about a longitudinal axis of the engaging portion.

In further embodiments, at least a portion of the plurality of struts of the engaging portion form a plurality of generally chevron shaped apertures in the proximal portion and the distal portion of the engaging portion. A proximal end of the proximal portion may be connected to the distal end of the body by connecting at least one longitudinally extending strut of the proximal portion with at least one longitudinally extending strut of the body. A proximal end of the distal portion may be connected to a distal end of the proximal portion by connecting at least one longitudinally extending strut of the proximal portion with at least one longitudinally extending strut of the distal portion.

In a still further embodiment, a method for filtering a body lumen is described. The method includes providing an implantable lumen filter having a body with a proximal end, a distal end, and a generally tapered outer surface. The outer surface is formed by a plurality of struts. The plurality of struts form a plurality of apertures. The apertures are dimensioned to inhibit and/or lyse particulates of a selected size from passing through the apertures and are dimensioned to allow blood components smaller than the selected size to pass through the apertures. The distal end has a first outer dimension. The implantable lumen filter includes an engaging portion having a proximal end and a distal end. The proximal end is connected to a distal end of the body. The engaging portion includes a generally annular shape. The engaging portion is configured to engage an inner surface of a body lumen. The engaging portion and the body are transitionable from a collapsed state toward a deployed state. The method includes longitudinally elongating the body and the engaging portion such that the implantable lumen filter has a reduced dimension. The implantable lumen filter is delivered to a desired deployment site within the body lumen. The body and the engaging portion are longitudinally reduced such that the implantable lumen filter has an enlarged dimension and the engaging portion applies radial forces to an inner wall of the body lumen.

In some embodiments, after longitudinally reducing the body and the engaging portion, the body and the engaging portion are longitudinally elongated such that the implantable lumen filter has a reduced dimension and the implantable lumen filter is removed from the desired deployment site within the body lumen. In further embodiments, at least a portion of the engaging portion and the struts of the body include cobalt chromium and/or alloys thereof and at least a portion of the engaging portion and the struts of the body include a thrombo-resistant, anti-proliferative, and/or anti-inflammatory component. In still further embodiments, the implantable lumen filter is removed by the proximal end or distal end of the body.

In a yet further embodiment, an implantable lumen filter is described. The implantable lumen filter includes a body having a proximal end, a distal end, and a generally conically shaped concave outer surface. The outer surface is formed by a plurality of struts. The plurality of struts form a plurality of apertures having a distal portion and a proximal portion. The apertures of the distal portion are fewer than the apertures of the proximal portion. The apertures are dimensioned to inhibit passage of and/or to lyse particulates of a selected size and are dimensioned to allow blood components smaller than the selected size to pass through the apertures. The body being transitionable from a collapsed state toward a deployed state. The implantable lumen filter includes an engaging portion configured to engage an inner surface of a body lumen.

In some embodiments, the plurality of apertures include an intermediate portion. The apertures of the intermediate portion may be fewer than the apertures of the proximal portion. The apertures of the intermediate portion may be greater than the apertures of the distal portion. In further embodiments, the apertures of the distal portion may be larger than the apertures of the intermediate portion. The apertures of the intermediate portion may be larger than the apertures of the proximal portion. In still further embodiments, at least a portion of the plurality of apertures are diamond shaped. In still further embodiments, the apertures of the distal portion are larger than the apertures of the proximal portion.

The implantable lumen filter, in some embodiments, includes a retrieval portion configured to facilitate retrieval of the implantable lumen filter from the body lumen. In further embodiments, the engaging portion may include at least one tissue piercing portion configured to pierce at least a portion of the inner surface of the body lumen. In still further embodiments, the engaging portion may include at least one tissue engaging portion configured to engage but not pierce at least a portion of the inner surface of the body lumen.

In another embodiment, an implantable lumen filter is described. The implantable lumen filter may include a body having a proximal end, a distal end, and a generally conically shaped concave outer surface. The outer surface is formed by a plurality of struts. The plurality of struts form a plurality of apertures having a distal portion and a proximal portion. The apertures of the distal portion are larger than the apertures of the proximal portion. The apertures are dimensioned to inhibit passage of and/or to lyse particulates of a selected size and are dimensioned to allow blood components smaller than the selected size to pass through the apertures. The body is transitionable from a collapsed state toward a deployed state. The implantable lumen filter includes an engaging portion configured to engage an inner surface of a body lumen.

In some embodiments, the plurality of apertures may include an intermediate portion. The apertures of the distal portion may be larger than the apertures of the intermediate portion. The apertures of the intermediate portion may be larger than the apertures of the proximal portion. In further embodiments, the apertures of the distal portion may be fewer than the apertures of the intermediate portion. The apertures of the intermediate portion may be fewer than the apertures of the proximal portion.

At least a portion of the plurality of apertures, in some embodiments, are generally chevron shaped. In further embodiments, the implantable lumen filter may include a retrieval portion configured to facilitate retrieval of the implantable lumen filter from the body lumen.

In a further embodiment, an implantable lumen filter is described. The implantable lumen filter includes a body having a proximal end, a distal end, and an outer surface formed by a plurality of struts. The plurality of struts form a plurality of apertures. The apertures are dimensioned to inhibit passage of and/or lyse particulates of a selected size and are dimensioned to allow blood components smaller than the selected size to pass through the apertures. The implantable lumen filter includes an engaging portion. The engaging portion includes a tissue piercing portion having a base portion and a piercing portion. The tissue piercing portion is configured to limit movement of the implantable filter within a body lumen. The engagement portion includes a tissue engaging portion connected to and surrounding the tissue piercing portion. The tissue engaging portion has sufficient surface area to limit movement of the implantable lumen filter toward a longitudinal axis of the body lumen. The tissue engaging portion cooperates with the tissue piercing portion to limit movement of the implantable filter within a body lumen.

In some embodiments, the tissue engaging portion may be generally elliptically shaped. In further embodiments, the tissue engaging portion may be generally polygonally shaped.

The tissue engaging portion and the tissue piercing portion, in some embodiments, may be formed from a single piece of material. In further embodiments, the tissue piercing portion may be formed by bending the tissue piercing portion from the base portion. In still further embodiments, the engaging portion may be connected to the implantable lumen filter near a proximal end of the body of the implantable lumen filter.

A still further embodiment of an implantable lumen filter is described. The implantable lumen filter includes a body having a proximal end, a distal end, and an outer surface formed by a plurality of struts. The plurality of struts form a plurality of apertures. The apertures are dimensioned to inhibit passage of and/or to lyse particulates of a selected size and are dimensioned to allow blood components smaller than the selected size to pass through the apertures. The filter includes a retrieval portion configured to facilitate retrieval of the implantable lumen filter from the body lumen. The retrieval portion is connected to the body. The retrieval portion has a proximal end and a distal end. The retrieval portion includes a retrieval surface. A portion of the retrieval surface is perpendicular to a longitudinal axis of a body lumen. The retrieval portion includes a connecting portion configured to connect the retrieval portion to the implantable lumen filter. The retrieval portion includes a receiving portion associated with the retrieval surface. The receiving portion is configured to receive the connecting portion. The receiving portion has a retaining portion defined by at least one expanded portion configured to limit movement of the connecting portion.

In some embodiments, the connecting portion may be connected to the distal end of the body. In further embodiments, the connecting portion may be connected to the proximal end of the body.

An embodiment of a method for filtering a body lumen is described. The method includes providing an implantable lumen filter. The implantable lumen filter includes a body having a proximal end, a distal end, and a generally conically shaped concave outer surface. The outer surface is formed by a plurality of struts. The plurality of struts form a plurality of apertures having a distal portion and a proximal portion. The apertures of the distal portion are fewer and/or larger than the apertures of the proximal portion. The apertures are dimensioned to inhibit passage of and/or to lyse particulates of a selected size from passing through the apertures and are dimensioned to allow blood components smaller than the selected size to pass through the apertures. The body is transitionable from a collapsed state toward a deployed state. The implantable lumen filter includes an engaging portion configured to engage an inner surface of a body lumen. The method includes longitudinally elongating the body such that the body has a reduced dimension. The elongated body is delivered to a desired deployment site within the body lumen. The body is longitudinally reduced such that the body has an enlarged dimension and applies radial forces to an inner wall of the body lumen.

In some embodiments, the plurality of apertures may include an intermediate portion. The apertures of the intermediate portion may be fewer and/or larger than the apertures of the proximal portion and the apertures of the intermediate portion may be greater and/or smaller than the apertures of the distal portion.

In a yet further embodiment, a body lumen filter includes a body having a first end and a second end. The body is configured to move between a pre-deployed state and a deployed state in which in the deployed state the body has filtering openings defined therein. The body lumen filter also includes a plurality of arcuate anchors distributed about at least a portion of a periphery of the body between the first end and the second end when the body is in a deployed state.

A body lumen filter can also include a body with filtering openings defined therein, arcuate anchors distributed about a periphery of the body lumen filter, the arcuate anchors being configured to engage a body vessel at a deployment site with a force effective to maintain the body at the deployment site while having a surface area sufficient to prevent penetration of the rounded portions through an intimal layer of the body vessel while the body is in the deployed state at the deployment site.

These and other features will become more fully apparent from the following description and appended claims, or can be learned by the practice of these embodiments as set forth hereinafter.

BRIEF DESCRIPTION OF THE DRAWINGS

In order to describe the manner in which the above-recited and other advantages and features can be obtained, a more particular description will be rendered by reference to specific embodiments, which are illustrated in the appended drawings. Understanding that these drawings depict only typical embodiments and are not therefore to be considered to be limiting of the present disclosure's scope, the example embodiments will be described and explained with additional specificity and detail through the use of the accompanying drawings.

Figure 1:
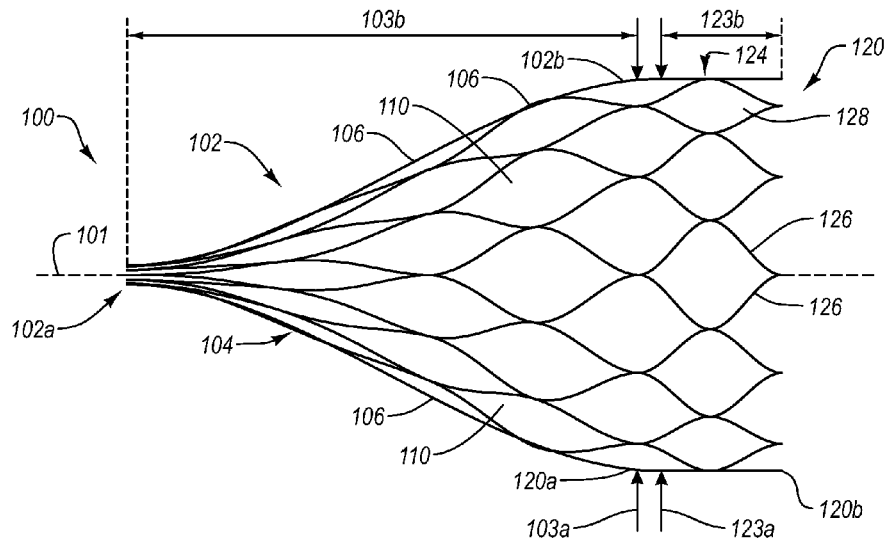
FIG. 1 illustrates an embodiment of an implantable lumen filter with an engaging portion.

It should be noted that the figures are not drawn to scale and that elements of similar structures or functions are generally represented by like reference numerals for illustrative purposes throughout the figures. It also should be noted that the figures are only intended to facilitate the description of example embodiments of the present disclosure.

DETAILED DESCRIPTION

The embodiments described herein extend generally to methods and apparatuses for filtering a body lumen. By way of example only, a body lumen may include a blood vessel. Filtering may be performed by implantable lumen filters. For instance, embodiments of implantable lumen filters (e.g. including vena cava and/or other lumen filters), are described. Components of implantable filters also are described. These components may include engagement portions, retrieval portions, and/or other components.

Pulmonary emboli reportedly cause up 120,000 deaths each year in the United States. An implantable lumen filter, when placed in the inferior vena cava may prevent emboli from reaching the pulmonary artery.

Some implantable lumen filters may be designed to capture and/or lyse particles of a particular size. Embodiments of the present invention may allow a distribution of particle shapes and/or sizes to be captured and/or lysed. For example, embodiments of an implantable lumen filter may be designed to capture and/or lyse larger particles (i.e. larger sized, larger in cross-sectional area, and/or otherwise larger) in a portion of the implantable lumen filter and smaller particles (i.e. smaller sized, smaller in cross-sectional area, and/or otherwise smaller) in another portion of the implantable lumen filter.

Thus, embodiments of the invention relating to methods and apparatus for filtering a body lumen may be useful for facilitating filtering of a body lumen.

The implantable lumen filters and/or any portions thereof as described herein may be manufactured from any suitable material. For example, an implantable lumen filter and/or engaging portion may be, at least partially, formed from various materials including nickel titanium and/or alloys thereof, cobalt chromium and/or alloys thereof, other materials including various implantable polymers, and/or combinations thereof. These materials may include at least one beneficial agent incorporated into the material and/or coated over at least a portion of the material.

The beneficial agents may be applied to implantable lumen filters that have been coated with a polymeric compound. Incorporation of the compound or drug into the polymeric coating of the implantable lumen filter can be carried out by dipping the polymer-coated implantable lumen filter into a solution containing the compound or drug for a sufficient period of time (such as, for example, five minutes) and then drying the coated implantable lumen filter, preferably by means of air drying for a sufficient period of time (such as, for example, 30 minutes). The polymer-coated implantable lumen filter containing the beneficial agent may then be delivered to a body vessel.

The pharmacologic agents that can be effective in preventing restenosis can be classified into the categories of anti-proliferative agents, anti-platelet agents, anti-inflammatory agents, anti-thrombotic agents, and thrombolytic agents. Anti-proliferative agents may include, for example, crystalline rapamycin. These classes can be further subdivided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

One or more immunosuppressant agents may be used. Immunosuppressant agents may include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAM tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins. In addition, a crystalline rapamycin analog, A-94507, SDZ RAD (a.k.a. Everolimus), and/or other immunosuppressants.

The implantable lumen filters may include hooks and/or other anchoring devices that pierce the inner wall of the body lumen to prevent filter migration. In some cases, piercing the inner wall of the body lumen may not be desirable. For instance, where the body lumen is already weakened. Implantable lumen filters that do not include hooks and/or other anchoring devices that pierce the inner wall of the body lumen may be subject to filter migration.

Some embodiments of implantable lumen filters described herein may include a generally cylindrical portion of an engagement member. The engagement member may be connected to an end of an implantable lumen filter. The engagement member may be sized and dimensioned to impart a radial force to the inner surface of the body lumen, align the implantable lumen filter within the body lumen, and/or provide other benefits. Thus, embodiments relating to an implantable lumen filter with an engaging portion and methods for filtering a body lumen may be useful for facilitating filtering of a body lumen.

FIG. 1 illustrates an embodiment of an implantable lumen filter 100 with an engaging portion 120. The implantable lumen filter 100 is shown in flattened form for ease of discussion. The implantable lumen filter 100 may include a body 102 having a proximal end 102a and a distal end 102b. The proximal end 102a may be the end of the body 102 that is closest to a user as the implantable lumen filter 100 is advanced into a body lumen. In other embodiments, the proximal end 102a may be the end of the body 102 that is farthest from a user. The body 102 may be transitionable from a compressed state toward an expanded state and is shown in FIG. 1 in the expanded state.

The body 102 may define an outer surface 104 that may be defined by a plurality of struts 106. The outer surface 104, in the present embodiment, may have a generally tapered shape from the proximal end 102a toward the distal end 102b. A generally tapered shape may include a line and/or curve tapered toward and rotated about a longitudinal axis 101, a generally right circular conic outer surface, a generally oblique conic outer surface, and/or other shapes that generally taper toward the one end.

The proximal end 102a, in the present embodiment, may be a generally more narrow portion of the implantable lumen filter 100 with the distal end 102b being a generally wider portion of the implantable lumen filter 100. Alternatively, the proximal end 102a may be a generally wider portion of the implantable lumen filter 100 with the distal end 102b being a more narrow portion of the implantable lumen filter 100.

The body 102 may include a first outer dimension 103a near the distal end 102b and/or a first longitudinal dimension 103b. The first longitudinal dimension 103b may extend from the proximal end 102a toward the distal end 102b generally parallel to the longitudinal axis 101.

The implantable lumen filter 100 may include an engaging portion 120 that may be configured to engage an inner surface of the body lumen. The engaging portion 120 may include an outer surface 124. The surface area and/or other features of the engaging portion 120, in the present embodiment, may be determined to facilitate engagement of the inner wall of the body lumen. For example, the outer surface 124 may have various textures to facilitate engagement. The engaging portion 120 may impart a radial force to an inner surface of a body lumen. In some embodiments, the engaging portion 120 may impart a radial force sufficient to anchor the implantable lumen filter 100 without piercing an inner surface of the body lumen.

The outer surface 124, in the present embodiment, may have a generally cylindrical shape from a proximal end 120a toward a distal end 120b. A generally cylindrical shape may allow for some non-uniformity. However, a generally cylindrical shape is typically more cylindrical than tapered, such as the taper of the body 102 shown in FIG. 1 compared to the non-uniformity of the engaging portion 120.

The engaging portion 120 may include a first outer dimension 123a near the distal end 120b and/or a first longitudinal dimension 123b. The first longitudinal dimension 103b may extend from the proximal end 102a toward the distal end 102b. The outer surface 124 may be defined by a plurality of struts 126. In other embodiments, the outer surface 124 may be otherwise defined. For example, the outer surface 124 may be defined by a substantially tubular piece of material.

The struts 106 of the body 102 and/or the struts 126 of the engaging portion 120 may be formed from various materials including nickel titanium and/or alloys thereof, copper chromium and/or alloys thereof, other materials, and/or combinations thereof. At least one beneficial agent may be incorporated into the material of and/or coated over at least a portion of the struts 106, 126. In embodiments where the body 102 and/or the engaging portion 120 are not defined by struts 106, 126, the material defining the body 102 and/or the engaging portion 120 may be formed from these various materials and/or may have at least one beneficial agent incorporated into the material of and/or coated over at least a portion of the material. For instance, an anti-thrombotic beneficial agent may be coated over at least a portion of the body 102.

The struts 106, 126 may form a plurality of apertures 110, 128 in the body 102 and/or the engaging portion 120, respectively. In the embodiment illustrated in FIG. 1, the struts 106, 126 form generally diamond shaped apertures 110, 128. The struts 106, 126 may form other shapes.

The struts 106, 126 may form apertures 110, 128 that are generally the same shape, for example generally diamond shaped. In other embodiments, the struts 106, 126 may form apertures 110, 128 that are different shapes, for example generally diamond shaped and generally chevron shaped. In further embodiments, the apertures 110, 128 may all be of varying shapes.

The struts 106, 126 may be welded and/or otherwise connected together. For example, a first ring of generally diamond shaped apertures 110, 128 may be formed by welding the struts 106, 126 together, a second ring and/or additional rings of generally diamond shaped apertures 110, 128 may be formed by welding the struts 106, 126 together, and then the various rings may be welded together. In other embodiments, the struts 106, 126 may be formed by removing material from the body 102 and/or the engaging portion 120 using, for example, laser cutting and/or other material removing procedures. In the present configuration, the engaging portion 120 may include a single ring of generally diamond shaped apertures 128.

The apertures 110, 128 may be spread across various portions of the body 102 and/or the engaging portion 120. The size and/or number of apertures 110, 128 may vary and may be selected to inhibit passage of and/or to lyse particulates of a selected size while allowing blood components smaller than the selected size to pass through said apertures. For instance, a distal portion of apertures 110, 128 may include generally larger and/or fewer apertures 110, 128 than an intermediate portion and/or proximal portion. Such a configuration may capture and/or lyse a variety of particles. In other embodiments, the apertures 110, 128 may be distributed over more and/or fewer portions.

The engaging portion 120 may be operatively connected to the body 102. For example, the struts 126 of the engaging portion 120 may be connected to the struts 106 of the body 102. The engaging portion 120 may be connected to the body 102 such that the body 102 and the engaging portion 120 share a generally common longitudinal axis 101. For example, the first outer dimension 103a of the body 102 may be approximately the same as the first outer dimension 123b of the engaging portion 120. As shown in FIG. 1, the first outer dimension 103a of the body 102 is shown as being relatively smaller than the first outer dimension 123b of the engaging portion 120. As discussed above, a generally cylindrical shape may allow for some non-uniformity. In some embodiments, the first outer dimension 103a of the body 102 may be within about five percent of the first outer dimension 123b of the engaging portion 120.

The engaging portion 120 may be dimensioned and configured to generally align the implantable lumen filter 100 within a body lumen. The engaging portion 120 may facilitate alignment within the body lumen by increasing surface area of the implantable lumen filter 100 distally of the distal end 102b of the body 102, by increasing the radial force applied by the implantable lumen filter 100, by other features, and/or combinations of the same.

In addition, the implantable lumen filter 100 may include one or more elements or components of the implantable lumen filters 200, 300, 400, 500, 600, 700, 800, 1100, 1200, 1300, 1400, 1500, 1700, 1900, 2000 illustrated in FIGS. 2-8 and 11-20 and described in more detail below. In further embodiments, the implantable lumen filter 100 may include the engagement portion 920 and/or retrieval portion 1030 illustrated in FIGS. 9-10, respectively, and described in more detail below.

Figure 2:
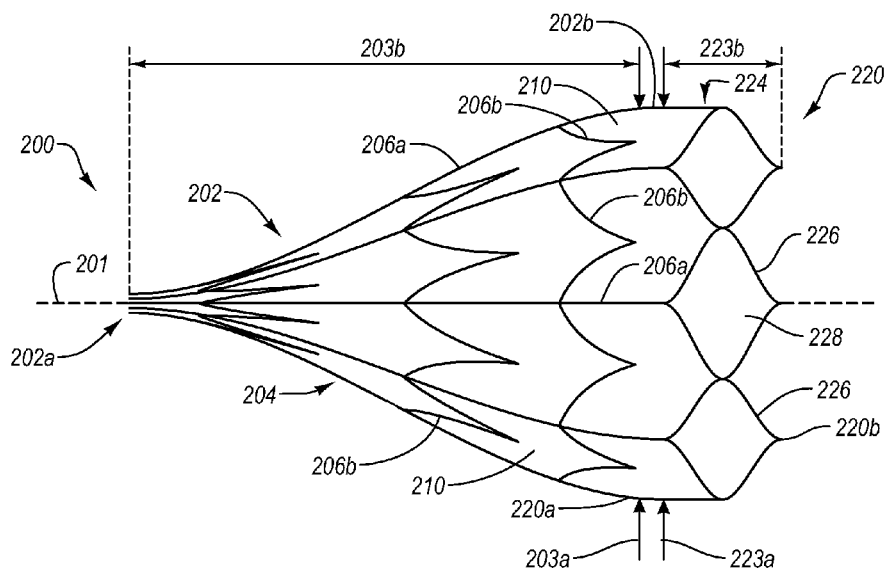
FIG. 2 illustrates another embodiment of an implantable lumen filter with an engaging portion.

FIG. 2 illustrates another embodiment of an implantable lumen filter 200 with an engaging portion 220. The implantable lumen filter 200 is shown in flattened form for ease of discussion. The implantable lumen filter 200 and/or engaging portion 220 of this other embodiment may be functionally similar to the implantable lumen filter 100 and/or engaging portion 120 previously described above and shown in FIG. 1 in most respects, wherein certain features will not be described in relation to this embodiment wherein those components may function in the manner as described above and are hereby incorporated into this alternative embodiment described below. Like structures and/or components are given like reference numerals.

The implantable lumen filter 200 may include a body 202 having a proximal end 202a and a distal end 202b. The body 202 may be transitionable from a compressed state toward an expanded state and is shown in the FIG. 2A in the expanded state.

The body 202 may define an outer surface 204 that may be defined by a plurality of struts 206a, 206b. In the present embodiment, the struts 206a extend from the distal end 202b toward the proximal end 202a generally in parallel to a longitudinal axis 201 and struts 206b may intersect the longitudinally extending struts 206a. The outer surface 204, in the present embodiment, may have a generally tapered shape from a proximal end 202a toward a distal end 202b.

The body 202 may include a first outer dimension 203a near the distal end 202b and/or a first longitudinal dimension 203b. The first longitudinal dimension 203b may extend from the proximal end 202a toward the distal end 202b generally parallel to the longitudinal axis 201.

The implantable lumen filter 200 may include an engaging portion 220 that may be configured to engage an inner surface of the body lumen. The engaging portion 220 may include an outer surface 224. The surface area and/or other features of the engaging portion 220 may be determined to facilitate engagement of the inner wall of the body lumen. For example, the outer surface 224 may have various textures to facilitate engagement. The engaging portion 220 may impart a radial force to an inner surface of a body lumen. In some embodiments, the engaging portion 220 may impart a radial force sufficient to anchor the implantable lumen filter 200 without piercing an inner surface of a body lumen.

The outer surface 224, in the present embodiment, may have a generally cylindrical shape from a proximal end 220a toward a distal end 220b. The engaging portion 220 may include a first outer dimension 223a near the distal end 220b and/or a first longitudinal dimension 223b. The first longitudinal dimension 203b may extend from the proximal end 202a toward the distal end 202b. The outer surface 224 may be defined by a plurality of struts 226. In other embodiments, the outer surface 224 may be otherwise defined. For example, the outer surface 224 may be defined by a substantially tubular piece of material.

The struts 206a, 206b of the body 202 and/or the struts 226 of the engaging portion 220 may be formed from various materials including nickel titanium and/or alloys thereof, copper chromium and/or alloys thereof, other materials, and/or combinations thereof. At least one beneficial agent may be incorporated into the material of and/or coated over at least a portion of the struts 206a, 206b, 226. In embodiments where the body 202 and/or the engaging portion 220 are not defined by struts 206a, 206b, 226, the material defining the body 202 and/or the engaging portion 220 may be formed from these various materials and/or may have at least one beneficial agent incorporated into the material of and/or coated over at least a portion of the material.

The struts 206a, 206b of the body 202 may form a plurality of apertures 210. In the embodiment illustrated in FIG. 2, the struts 206a, 206b form generally chevron shaped apertures 210. For example, a pair of struts 206b may form a "V"-shaped web between two struts 206a. The struts 206a, 206b may form other shapes.

The struts 226 of the engaging portion 220 may form apertures 228 that are a different shape than the shape of the apertures 210 formed by the struts 206a, 206b of the body 202. For example, the apertures 228 of the engaging portion 220 may be generally diamond shaped. In other embodiments, the struts 206a, 206b, 226 may form apertures 210, 228 that are the same shape, for example generally diamond shaped, generally chevron shaped, and/or otherwise shaped. In further embodiments, the apertures 210, 228 may be of varying shapes.

The struts 206a, 206b of the body 202 and/or the struts 226 of the engaging portion 220 may be welded and/or otherwise connected together. For example, a first ring of generally chevron shaped apertures 210 may be formed by welding the struts 206a, 206b together, a second ring and/or additional rings of chevron or otherwise shaped apertures 210 may be formed by welding the struts 206a, 206b together, and then the various rings may be welded together. For instance, the struts 206a of the first ring may be connected to the struts 206a of the second ring. In another example, a first ring of generally diamond shaped apertures 228 may be formed by welding the struts 226 of the engaging portion 220 together, a second ring and/or additional rings of generally diamond shaped apertures 228 may be formed by welding the struts 226 together, and then the various rings may be welded together. In other embodiments, the struts 206a, 206b, 226 may be formed by removing material from the body 202 and/or the engaging portion 220 using, for example, laser cutting and/or other material removing procedures. In the present configuration, the engaging portion 220 may include a single ring of generally diamond shaped apertures 228.

The apertures 210, 228 may be spread across various portions of the body 202 and/or the engaging portion 220. The size and/or number of apertures 210, 228 may vary and may be selected to inhibit passage of and/or to lyse particulates of a selected size while allowing blood components smaller than the selected size to pass through said apertures. For instance, a distal portion of apertures 210, 228 may include generally larger and/or fewer apertures 210, 228 than an intermediate portion and/or proximal portion. Such a configuration may capture and/or lyse a variety of particles. In other embodiments, the apertures 210, 228 may be distributed over more and/or fewer portions.

The struts 206a, 206b and/or other portions of the body 202 may be used to retrieve the filter 200 after it has been deployed. For example, the "V"-shape formed by the struts 206b may be engaged by a retrieval member, such as a hook, to retrieve the filter 200.

The engaging portion 220 may be operatively connected to the body 202. For example, the struts 226 of the engaging portion 220 may be connected to the struts 206a, 206b of the body 202. The engaging portion 220 may be connected to the body 202 such that the body 202 and the engaging portion 220 share a generally common longitudinal axis 201. The engaging portion 220 may be dimensioned and configured to generally align the implantable lumen filter 200 within a body lumen. The engaging portion 220 may facilitate alignment within the body lumen by increasing surface area of the implantable lumen filter 200 distally of the distal end of the body 202, by increasing the radial force applied by the implantable lumen filter 200, by other features, and/or combinations of the same.

In addition, the implantable lumen filter 200 may include one or more elements or components of the implantable lumen filters 300, 400, 500, 600, 700, 800, 1100, 1200, 1300, 1400, 1500, 1700, 1900, 2000 illustrated in FIGS. 3-8 and 11-20 and described in more detail below. In further embodiments, the implantable lumen filter 200 may include the engagement portion 920 and/or retrieval portion 1030 illustrated in FIGS. 9-10, respectively, and described in more detail below.

Figure 3:
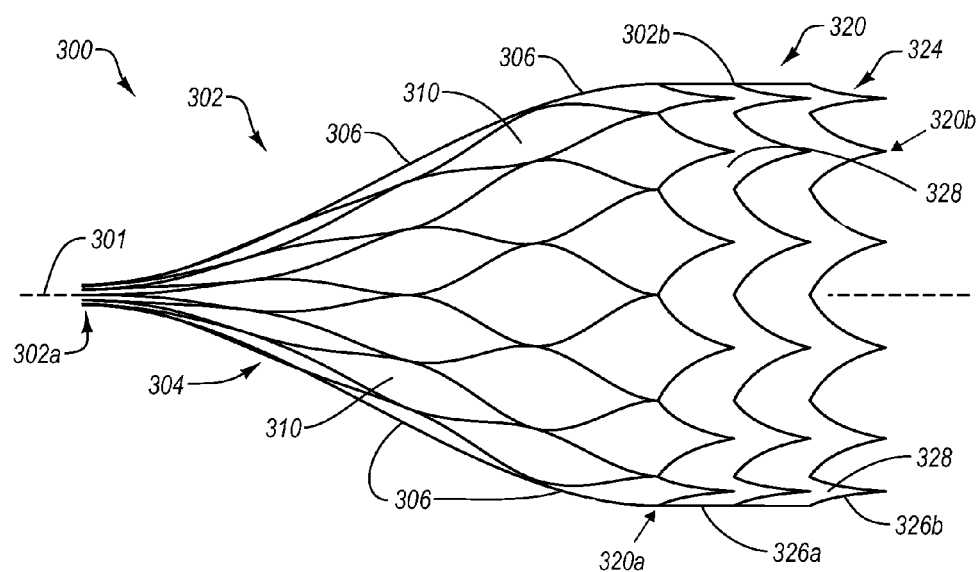
FIG. 3 illustrates a further embodiment of an implantable lumen filter with an engaging portion.

FIG. 3 illustrates a further embodiment of an implantable lumen filter 300 with an engaging portion 320. The implantable lumen filter 300 is shown in flattened form for ease of discussion. The implantable lumen filter 300 and/or engaging portion of 320 of this further embodiment may be functionally similar to the implantable lumen filters 100, 200 and/or engaging portions 120, 220 previously described above and shown in FIGS. 1-2 in most respects, wherein certain features will not be described in relation to this embodiment wherein those components may function in the manner as described above and are hereby incorporated into this alternative embodiment described below. Like structures and/or components are given like reference numerals.

The implantable lumen filter 300 may include a body 302 having a proximal end 302a and a distal end 302b. The body 302 may be transitionable from a compressed state toward an expanded state and is shown in the FIG. 3 in the expanded state.

The body 302 may define an outer surface 304 that may be defined by a plurality of struts and 306. The outer surface 304, in the present embodiment, may have a generally tapered shape from the proximal end 302a toward the distal end 302b.

The implantable lumen filter 300 may include an engaging portion 320 that may be configured to engage an inner surface of the body lumen. The surface area and/or other features of the engaging portion 320, in the present configuration, may be determined to facilitate engagement of the inner wall of the body lumen. The engaging portion 320 may impart a radial force to an inner surface of a body lumen. In some embodiments, the engaging portion 320 may impart a radial force sufficient to anchor the implantable lumen filter 300 without piercing an inner surface of the body lumen. The body 302 and/or engaging portion 320 may include first outer dimensions (not shown) and/or first longitudinal dimensions (not shown).

The engaging portion 320 may include an outer surface 324. The outer surface 324 may have a generally cylindrical shape from a proximal end 320a toward a distal end 320b. The outer surface 324 may be defined by a plurality of struts 326a, 326b. In the present configuration, the struts 306a extend from the distal end 302b toward the proximal end 302a generally in parallel to a longitudinal axis 301 and struts 306b may intersect the longitudinally extending struts 306a. In other embodiments, the outer surface 324 may be otherwise defined. For example, the outer surface 324 may be defined by a substantially tubular piece of material.

The struts 306 of the body 302 and/or the struts 326a, 326b of the engaging portion 320 may be formed from various materials including nickel titanium and/or alloys thereof, copper chromium and/or alloys thereof, other materials, and/or combinations thereof. At least one beneficial agent may be incorporated into the material of and/or coated over at least a portion of the struts 306, 326a, 326b. In embodiments where the body 302 and/or the engaging portion 320 are not defined by struts 306, 326a, 326b, the material defining the body 302 and/or the engaging portion 320 may be formed from these various materials and/or may have at least one beneficial agent incorporated into the material of and/or coated over at least a portion of the material.

The struts 306 of the body 302 may form a plurality of apertures 310. In the embodiment illustrated in FIG. 3, the struts 306 form generally diamond shaped apertures 310. The struts 306 may form other shapes.

The struts 326a, 326b of the engaging portion 320 may form apertures 328 that are a different shape than the shape of the apertures 310 formed by the struts 306 of the body 302. For example, the apertures 328 of the engaging portion 320 may be generally chevron shaped. In other embodiments, the struts 306, 326a, 326b may form apertures 310, 328 that are the same shape, for example generally diamond shaped, generally chevron shaped, and/or otherwise shaped. In further embodiments, the apertures 310, 328 may be of varying shapes.

The struts 306 of the body 302 and/or the struts 326a, 326b of the engaging portion 320 may be welded and/or otherwise connected together. For example, a first ring of generally diamond shaped apertures 310 may be formed by welding the struts 306 together, a second ring and/or additional rings of diamond or otherwise shaped apertures 310 may be formed by welding the struts 306 together, and then the various rings may be welded together. In another example, a first ring of generally chevron shaped apertures 328 may be formed by welding the struts 326a, 326b of the engaging portion 320 together, a second ring and/or additional rings of generally chevron shaped apertures 328 may be formed by welding the struts 326a, 326b together, and then the various rings may be welded together. For instance, the struts 326a of the first ring may be connected to the struts 326a of the second ring. In other embodiments, the struts 306, 326a, 326b may be formed by removing material from the body 302 and/or the engaging portion 320 using, for example, laser cutting and/or other material removing procedures. In the present configuration, the engaging portion 320 may include a single ring of generally chevron shaped apertures 328.

The apertures 310, 328 may be spread across various portions of the body 302 and/or the engaging portion 320. The size and/or number of apertures 310, 328 may vary and may be selected to inhibit passage of and/or to lyse particulates of a selected size while allowing blood components smaller than the selected size to pass through said apertures.

The engaging portion 320 may be operatively connected to the body 302. For example, the struts 326a, 326b of the engaging portion 320 may be connected to the struts 306 of the body 302. The engaging portion 320 may be connected to the body 302 such that the body 302 and the engaging portion 320 share a generally common longitudinal axis 301. The engaging portion 320 may be dimensioned and configured to generally align the implantable lumen filter 300 within a body lumen. The engaging portion 320 may facilitate alignment within the body lumen by increasing surface area of the implantable lumen filter 300 distally of the distal end of the body 302, by increasing the radial force applied by the implantable lumen filter 300, by other features, and/or combinations of the same.

In addition, the implantable lumen filter 300 may include one or more elements or components of the implantable lumen filters 400, 500, 600, 700, 800, 1100, 1200, 1300, 1400, 1500, 1700, 1900, 2000 illustrated in FIGS. 4-8 and 11-20 and described in more detail below. In further embodiments, the implantable lumen filter 300 may include the engagement portion 920 and/or retrieval portion 1030 illustrated in FIGS. 9-10, respectively, and described in more detail below.

Figure 4:
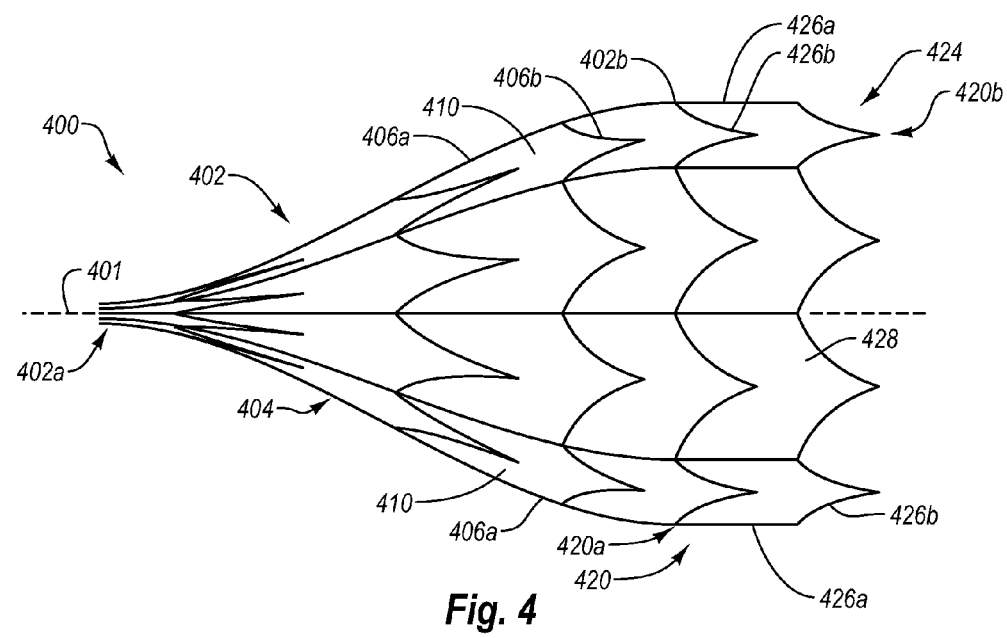
FIG. 4 illustrates a still further embodiment of an implantable lumen filter with an engaging portion.

FIG. 4 illustrates a still further embodiment of an implantable lumen filter 400 with an engaging portion 420. The implantable lumen filer 400 is shown in flattened form for each of discussion. The implantable lumen filter 400 and/or engaging portion of 420 of this further embodiment may be functionally similar to the implantable lumen filters 100, 200, 300 and/or engaging portions 120, 220, 320 previously described above and shown in FIGS. 1-3 in most respects, wherein certain features will not be described in relation to this embodiment wherein those components may function in the manner as described above and are hereby incorporated into this alternative embodiment described below. Like structures and/or components are given like reference numerals.

The implantable lumen filter 400 may include a body 402 having a proximal end 402a and a distal end 402b. The body 402 may be transitionable from a compressed state toward an expanded state and is shown in the FIG. 4 in the expanded state.

The body 402 may define an outer surface 404 that may be defined by a plurality of struts and 406a, 406b. In the present embodiment, the struts 406a extend from the distal end 402b toward the proximal end 402a generally in parallel to a longitudinal axis 401 and struts 406b may intersect the longitudinally extending struts 406a. The outer surface 404, in the present embodiment, may have a generally tapered shape from a proximal end 402a toward a distal end 402b.

The implantable lumen filter 400 may include an engaging portion 420 that may be configured to engage an inner surface of the body lumen. The surface area and/or other features of the engaging portion 420, in the present configuration, may be determined to facilitate engagement of the inner wall of the body lumen. The engaging portion 420 may impart a radial force to an inner surface of the body lumen. In some embodiments, the engaging portion 420 may impart a radial force sufficient to anchor the implantable lumen filter 400 without piercing the inner surface of the body lumen. The body 402 and/or engaging portion 420 may include first outer dimensions (not shown) and/or first longitudinal dimensions (not shown).

The engaging portion 420 may include an outer surface 424. The outer surface 424 may have a generally cylindrical shape from a proximal end 420a toward a distal end 420b. The outer surface 424 may be defined by a plurality of struts 426a, 426b. In the present embodiment, the struts 406a extend from the distal end 402b toward the proximal end 402a generally in parallel to a longitudinal axis 401 and struts 406b may intersect the longitudinally extending struts 406a. In other embodiments, the outer surface 424 may be otherwise defined. For example, the outer surface 424 may be defined by a substantially tubular piece of material.

The struts 406a, 406b of the body 402 and/or the struts 426a, 426b of the engaging portion 420 may be formed from various materials including nickel titanium and/or alloys thereof, copper chromium and/or alloys thereof, other materials, and/or combinations thereof. At least one beneficial agent may be incorporated into the material of and/or coated over at least a portion of the struts 406a, 406b, 426a, 426b.

The struts 406a, 406b of the body 402 may form a plurality of apertures 410. In the embodiment illustrated in FIG. 4, the struts 406a, 406b form generally chevron shaped apertures 410. For example, a pair of struts 406b may form a "V"-shaped web between two struts 406a. The struts 406a, 406b may form other shapes.

The struts 406a, 406b, 426a, 426b may form apertures 428 that are generally the same shape, for example generally chevron shaped. In other embodiments, the struts 406a, 406b, 426a, 426b may form apertures 410, 428 that are the different shapes, for example generally diamond shaped, generally chevron shaped, and/or otherwise shaped. In further embodiments, the apertures 410, 428 may be of varying shapes.

The struts 406a, 406b of the body 402 and/or the struts 426a, 426b of the engaging portion 420 may be welded and/or otherwise connected together. For example, a first ring of generally chevron shaped apertures 410 may be formed by welding the struts 406a, 406b together, a second ring and/or additional rings of chevron or otherwise shaped apertures 410 may be formed by welding the struts 406a, 406b together, and then the various rings may be welded together. For instance, the struts 406a of the first ring may be connected to the struts 406a of the second ring. In another example, a first ring of generally chevron shaped apertures 428 may be formed by welding the struts 426a, 426b of the engaging portion 420 together, a second ring and/or additional rings of generally chevron shaped apertures 428 may be formed by welding the struts 426a, 426b together, and then the various rings may be welded together. For instance, the struts 426a of the first ring may be connected to the struts 426a of the second ring. In other embodiments, the struts 406a, 406b, 426a, 426b may be formed by removing material from the body 402 and/or the engaging portion 420 using, for example, laser cutting and/or other material removing procedures. In the present configuration, the engaging portion 420 may include a single ring of generally chevron shaped apertures 428.

In embodiments where the apertures 410, 428 are generally the same shape, the distal-most ring of apertures 410 in the body may interact with the proximal-most ring of apertures 428 in the engaging portion 420 to form an additional ring of a similar shape (i.e. chevron shaped in FIG. 4 or diamond shaped in FIG. 1). In embodiments where the apertures 410, 428 generally differ in shape, the distal-most ring of apertures 410 in the body may interact with the proximal-most ring of apertures 428 in the engaging portion 420 to form a hybrid shaped ring (i.e. a skewed chevron shape in FIG. 2 or a generally diamond shape with a concave distal portion in FIG. 3).

The apertures 410, 428 may be spread across various portions of the body 402 and/or the engaging portion 420. The size and/or number of apertures 410, 428 may vary and may be selected to inhibit passage of and/or to lyse particulates of a selected size while allowing blood components smaller than the selected size to pass through said apertures.

The engaging portion 420 may be operatively connected to the body 402. For example, the struts 426a, 426b of the engaging portion 420 may be connected to the struts 406a, 406b of the body 402. The engaging portion 420 may be connected to the body 402 such that the body 402 and the engaging portion 420 share a generally common longitudinal axis 401. The engaging portion 420 may be dimensioned and configured to generally align the implantable lumen filter 400 within a body lumen. The engaging portion 420 may facilitate alignment within the body lumen by increasing the surface area of the implantable lumen filter 400 distally of the distal end of the body 402, by increasing the radial force applied by the implantable lumen filter 400, by other features, and/or combinations of the same.

In addition, the implantable lumen filter 400 may include one or more elements or components of the implantable lumen filters 500, 600, 700, 800, 1100, 1200, 1300, 1400, 1500, 1700, 1900, 2000 illustrated in FIGS. 5-8 and 11-20 and described in more detail below. In further embodiments, the implantable lumen filter 400 may include the engagement portion 920 and/or retrieval portion 1030 illustrated in FIGS. 9-10, respectively, and described in more detail below.

Figure 5:
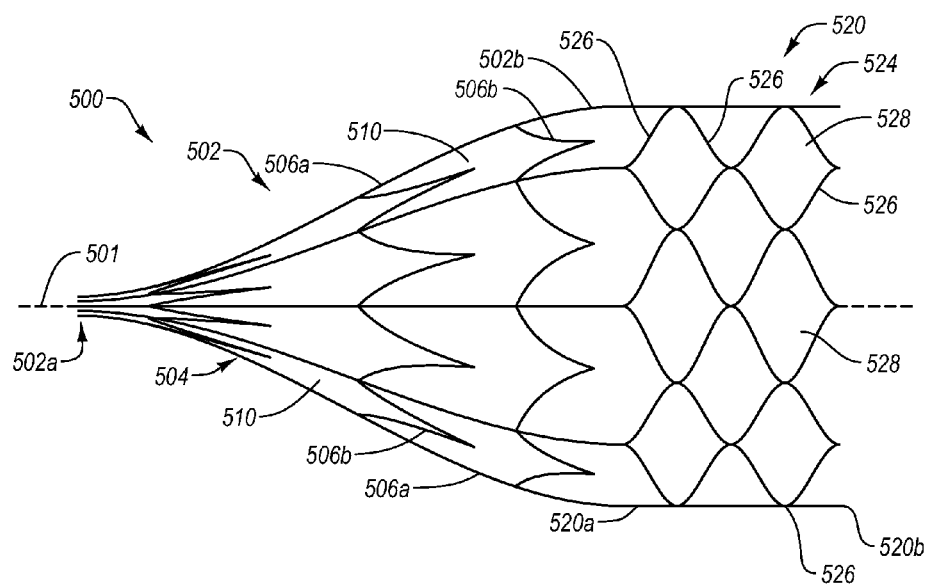
FIG. 5 illustrates a yet further embodiment of an implantable lumen filter with an engaging portion.

FIG. 5 illustrates a yet further embodiment of an implantable lumen filter 500 with an engaging portion 520. The implantable lumen filter 500 is shown in flattened form for ease of discussion. The implantable lumen filter 500 and/or engaging portion 520 of this other embodiment may be functionally similar to the implantable lumen filters 100, 200, 300, 400 and/or engaging portion 120, 220, 320, 420 previously described above and shown in FIGS. 1-4 in most respects, wherein certain features will not be described in relation to this embodiment wherein those components may function in the manner as described above and are hereby incorporated into this alternative embodiment described below. Like structures and/or components are given like reference numerals.

The apertures 528 of the engaging portion 520, as illustrated in FIG. 5, may be generally diamond shaped compared with the generally chevron shaped apertures 510 of the body 502. In other embodiments, the apertures 510, 528 may have other shapes or may have generally the same shape.

The implantable lumen filter 500 may include an additional ring of apertures 528. For example, the engaging portion 520 may include at least two rings of apertures 528. In other embodiments, more and/or fewer rings of apertures 528 may be included.

In addition, the implantable lumen filter 500 may include one or more elements or components of the implantable lumen filters 600, 700, 800, 1100, 1200, 1300, 1400, 1500, 1700, 1900, 2000 illustrated in FIGS. 6-8 and 11-20 and described in more detail below. In further embodiments, the implantable lumen filter 500 may include the engagement portion 920 and/or retrieval portion 1030 illustrated in FIGS. 9-10, respectively, and described in more detail below.

Figure 6A:
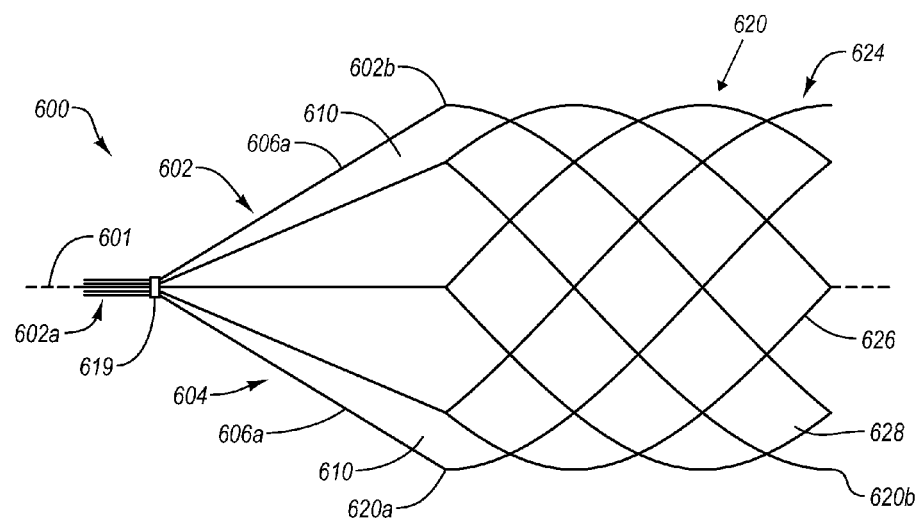
FIGS. 6A-6B illustrate another embodiment of an implantable lumen filter with an engaging portion.
Figure 6B:
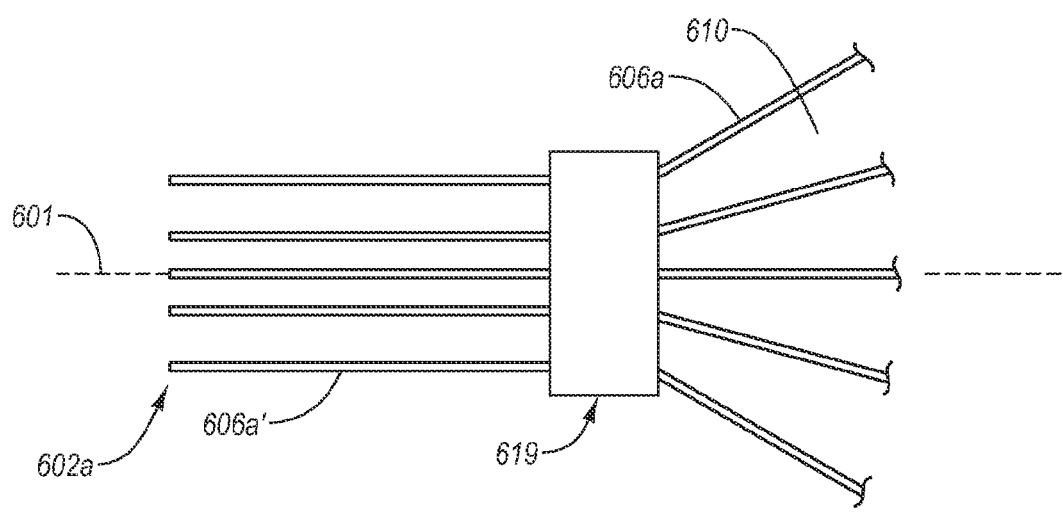

FIG. 6 illustrates another embodiment of an implantable lumen filter 600 with an engaging portion 620. The implantable lumen filter 600 is shown in flattened form for ease of discussion. The implantable lumen filter 600 and/or engaging portion 620 of this other embodiment may be functionally similar to the implantable lumen filters 100, 200, 300, 400, 500 and/or engaging portions 120, 220, 320, 420, 520 previously described above and shown in FIGS. 1-5 in most respects, wherein certain features will not be described in relation to this embodiment wherein those components may function in the manner as described above and are hereby incorporated into this alternative embodiment described below. Like structures and/or components are given like reference numerals.

The implantable lumen filter 600 may include a body 602 having a proximal end 602a and a distal end 602b. The body 602 may be transitionable from a compressed state toward an expanded state and is shown in the FIG. 6A in the expanded state.

The body 602 may define an outer surface 604 that may be defined by a plurality of struts 606a. In the present embodiment, the struts 606a extend from the distal end 602b toward the proximal end 602a generally in parallel to a longitudinal axis 601. The outer surface 604, in the present embodiment, may have a generally tapered shape from a proximal end 602a toward a distal end 602b.

The implantable lumen filter 600 may include an engaging portion 620 that may be configured to engage an inner surface of the body lumen. The engaging portion 620 may include an outer surface 624. The surface area and/or other features of the engaging portion 620 may be determined to facilitate engagement of the inner wall of the body lumen. For example, the outer surface 624 may have various textures to facilitate engagement. The engaging portion 620 may impart a radial force to an inner surface of a body lumen. In some embodiments, the engaging portion 620 may impart a radial force sufficient to anchor the implantable lumen filter 600 without piercing an inner surface of a body lumen.

The outer surface 624, in the present embodiment, may have a generally cylindrical shape from a proximal end 620a toward a distal end 620b. The outer surface 624 may be defined by a plurality of struts 626. In other embodiments, the outer surface 624 may be otherwise defined. For example, the outer surface 624 may be defined by a substantially tubular piece of material.

The struts 606a of the body 602 and/or the struts 626 of the engaging portion 620 may be formed from various materials including nickel titanium and/or alloys thereof, copper chromium and/or alloys thereof, other materials, and/or combinations thereof. At least one beneficial agent may be incorporated into the material of and/or coated over at least a portion of the struts 606a, 626. In embodiments where the body 602 and/or the engaging portion 620 are not defined by struts 606a, 626, the material defining the body 602 and/or the engaging portion 620 may be formed from these various materials and/or may have at least one beneficial agent incorporated into the material of and/or coated over at least a portion of the material.

The struts 606a of the body 602 may form a plurality of apertures 610. In the embodiment illustrated in FIG. 6, the struts 606a form generally triangular shaped apertures 610 from the distal end 602b toward the proximal end 602a. For example, a pair of struts 606a may form a "V"-shaped aperture 610. The struts 606a may form other shapes.

The struts 626 of the engaging portion 620 may form apertures 628 that are a different shape than the shape of the apertures 610 formed by the struts 606a of the body 602. For example, the apertures 628 of the engaging portion 620 may be generally diamond shaped. In other embodiments, the struts 606a, 626 may form apertures 610, 628 that are the same shape, for example generally diamond shaped, generally chevron shaped, generally triangular shaped, and/or otherwise shaped. In further embodiments, the apertures 610, 628 may be of varying shapes.

The struts 606a of the body 602 and/or the struts 626 of the engaging portion 620 may be welded and/or otherwise connected together. For example, a first ring of generally triangular shaped apertures 610 may be formed by connecting the struts 606a together near the proximal end 602a. In another example, the struts 606a of the first ring may be connected together using a ring 619. The ring 619 may be connected to the struts 606a by crimping, welding, and/or other connecting methods. In another example, the ring 619 and the struts 606a may be formed from the same material by, for example, laser cutting.

The ring 619 may be used to retrieve the filter 600 after it has been deployed. For example, a retrieval member, such as a hook, may engage the ring 619 to retrieve the filter 600.

In a further example, a first ring of generally diamond shaped apertures 628 may be formed by welding the struts 626 of the engaging portion 620 together, a second ring and/or additional rings of generally diamond shaped apertures 628 may be formed by welding the struts 626 together, and then the various rings may be welded together. In other embodiments, the struts 606a, 626 may be formed by removing material from the body 602 and/or the engaging portion 620 using, for example, laser cutting and/or other material removing procedures. In the present configuration, the engaging portion 620 may include two rings of generally diamond shaped apertures 628.

The apertures 610, 628 may be spread across various portions of the body 602 and/or the engaging portion 620. The size and/or number of apertures 610, 628 may vary and may be selected to inhibit passage of and/or to lyse particulates of a selected size while allowing blood components smaller than the selected size to pass through said apertures. For instance, a distal portion of apertures 628 may include generally larger and/or fewer apertures 628 than an intermediate portion and/or proximal portion. Such a configuration may capture and/or lyse a variety of particles. In other embodiments, the apertures 610, 628 may be distributed over more and/or fewer portions.

The engaging portion 620 may be operatively connected to the body 602. For example, the struts 626 of the engaging portion 620 may be connected to the struts 606a of the body 602. The engaging portion 620 may be connected to the body 602 such that the body 602 and the engaging portion 620 share a generally common longitudinal axis 601. The engaging portion 620 may be dimensioned and configured to generally align the implantable lumen filter 600 within a body lumen. The engaging portion 620 may facilitate alignment within the body lumen by increasing surface area of the implantable lumen filter 600 distally of the distal end of the body 602, by increasing the radial force applied by the implantable lumen filter 600, by other features, and/or combinations of the same.

The struts 606a of the body 602, in the present configuration, may be connected to a corresponding generally diamond shaped aperture 628 in the engaging portion 620. For example, as shown in FIG. 6A, each strut 606a is connected to the proximal end of a generally diamond shaped aperture 628, such that every generally diamond shaped aperture 628 is connected to a strut 606a. In other embodiments, fewer than each generally diamond shaped aperture 628 may be connected to a strut 606a. For instance, every other generally diamond shaped aperture 628 may be connected to a strut 606a.

The struts 606a of the body 602 may include a proximal portion 606a'. The struts 606a may be operatively connected by the proximal portion 606a'. For example, the struts 606a may be welded together in the proximal portion 606a'. In the present configuration, one or more struts 606a may be formed from the same piece of material. The struts 606a may be operatively connected by the ring 619.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

In addition, the implantable lumen filter 600 may include one or more elements or components of the implantable lumen filters 700, 800, 1100, 1200, 1300, 1400, 1500, 1700, 1900, 2000 illustrated in FIGS. 7-8 and 11-20 and described in more detail below. In further embodiments, the implantable lumen filter 600 may include the engagement portion 920 and/or retrieval portion 1030 illustrated in FIGS. 9-10, respectively, and described in more detail below.

Figure 7:
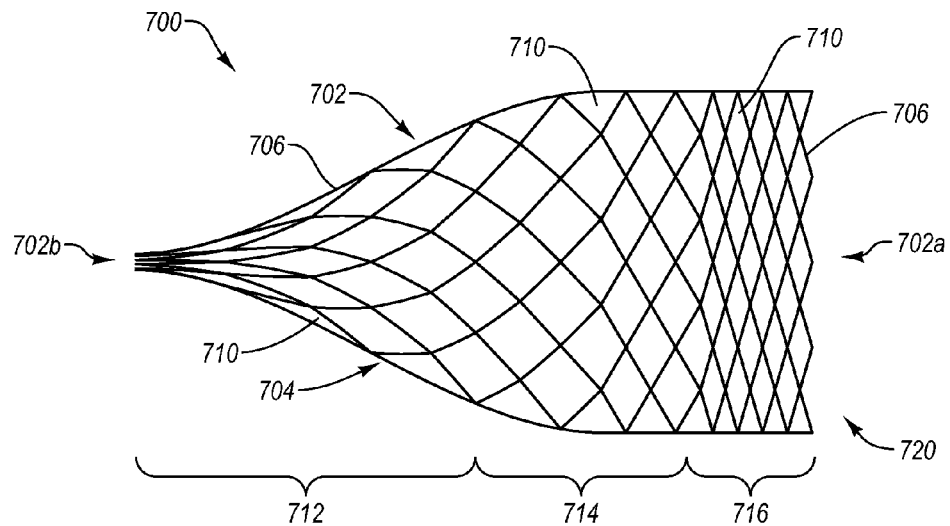
FIG. 7 is illustrates an embodiment of an implantable lumen filter.

FIG. 7 illustrates an embodiment of an implantable lumen filter 700. The implantable lumen filter 700 of this other embodiment may be functionally similar to the implantable lumen filters 100, 200, 300, 400, 500, 600 previously described above and shown in FIGS. 1-6 in most respects, wherein certain features will not be described in relation to this embodiment wherein those components may function in the manner as described above and are hereby incorporated into this alternative embodiment described below. Like structures and/or components may be given like reference numerals.

The implantable lumen filter 700 may include a body 702 having a proximal end 702a and a distal end 702b. The body 702 may be transitionable from a compressed state to an expanded state and is shown in the FIG. 7 in the expanded state.

The body 702 may define an outer surface 704 that may be defined by a plurality of struts 706. The struts 706 may be formed from various materials including nickel titanium and/or alloys thereof, implantable polymers, other materials, or combinations thereof. The outer surface 704, in the present embodiment, may have a generally concave conic shape from a base near the proximal and 702a toward an apex at the distal and 702b. A generally concave conic shape may include a curve generally defined by the equation $\tan(x)$ rotated about a longitudinal axis, a generally right circular conic outer surface with at least one concave portion that, in some embodiments, may be found near the distal end 702b, a generally oblique conic outer surface with at least one concave portion, and/or other shapes that are generally conic with a non-uniform taper toward the distal end 702b.

The struts 706 may form a plurality of apertures 710. In the embodiment illustrated in FIG. 7, the struts 706 form generally diamond shaped apertures 710. The struts 706 may form other shapes. The struts 706 may be welded or otherwise connected together. For example, a first ring of diamond shaped apertures 710 may be formed by welding the struts 706 together, a second ring and/or additional rings of diamond shaped apertures 710 may be formed by welding the struts 706 together, and then the various rings may be welded together. In other embodiments, the struts 706 may be formed by removing material from the body 702 using, for example, laser cutting and/or other material removing procedures.

The apertures 710 may be spread across various portions of the body 702. In the present embodiment, the apertures 710 may be distributed over a distal portion 712, an intermediate portion 714, and/or a proximal portion 716. The size and/or number of apertures 710 may vary between the various portions 712, 714, 716 and may be selected to inhibit passage of and/or to lyse particulates of a selected size while allowing blood components smaller than the selected size to pass through said apertures. For instance, the distal portion 712 may include generally larger and/or fewer apertures 710 than the intermediate portion 714 and/or the proximal portion 716, the intermediate portion 714 may include generally larger and/or fewer apertures 710 than the proximal portion 716, and/or the proximal portion 716 may include generally smaller and/or more apertures 710 than the intermediate portion 714 and/or the distal portion 712. Such a configuration may capture and/or lyse a variety of particles. In other embodiments, the apertures 710 may be distributed over more and/or fewer portions.

The body 702 may include an engaging portion 720 that may be configured to engage an inner surface of the body lumen. In the present embodiment, the engaging portion 720 may include a tissue engaging portion (not shown) that may include a portion, such as the proximal portion 716 of the outer surface 704. The portion may engage the inner surface of the body lumen. The surface area of the engaging portion 720, in the present embodiment, may be determined to facilitate engagement of the inner wall of the body lumen.

In addition, the implantable lumen filter 700 may include one or more elements or components of the implantable lumen filters 800, 1100, 1200, 1300, 1400, 1500, 1700, 1900, 2000 illustrated in FIGS. 8 and 11-20 and described in more detail below. In further embodiments, the implantable lumen filter 700 may include the engagement portion 920 and/or retrieval portion 1030 illustrated in FIGS. 9-10, respectively, and described in more detail below.

Figure 8:
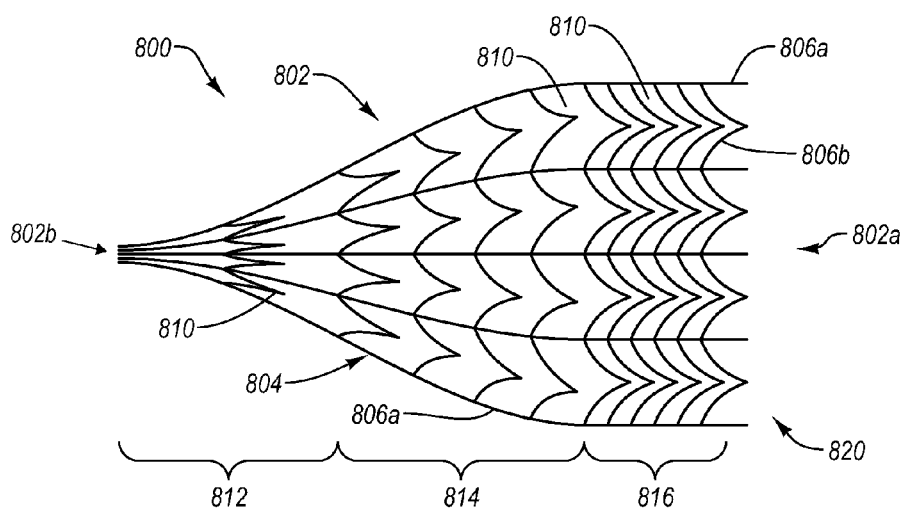
FIG. 8 illustrates another embodiment of an implantable lumen filter.

FIG. 8 illustrates another embodiment of an implantable lumen filter 800. The implantable lumen filter 800 of this other embodiment may be functionally similar to the implantable lumen filters 100, 200, 300, 400, 500, 600, 700 previously described above and shown in FIGS. 1-7 in most respects, wherein certain features will not be described in relation to this embodiment wherein those components may function in the manner as described above and are hereby incorporated into this alternative embodiment described below. Like structures and/or components may be given like reference numerals.

The implantable lumen filter 800 may include a body 802 having a proximal end 802a and a distal end 802b. The body 802 may be transitionable from a compressed state to an expanded state and is shown in the FIG. 8 in the expanded state.

The body 802 may define an outer surface 804 that may be defined by a plurality of struts 806a, 806b. In the present embodiment, extending struts 806a extend from the distal end 802b toward the proximal and 802a and intersecting struts 806b may intersect the extending struts 806a. The struts 806a, 806b may be formed from various materials including nickel titanium and/or alloys thereof. The outer surface 804, in the present embodiment, may have a generally concave conic shape from a base near the proximal and 802a toward an apex at the distal and 802b.

The struts 806a, 806b may form a plurality of apertures 810. In the embodiment illustrated in FIG. 8, the struts 806a, 806b form generally chevron shaped apertures 810. For example, a pair of intersecting struts 806b may form a "V"-shaped web between two extending struts 806a. The struts 806a, 806b may form other shapes. In the present embodiment, the struts 806a, 806b may be welded or otherwise connected together. For example, the extending struts 806a may be welded together near the distal end 802b while the intersecting struts 806b may be welded to the extending struts 806b. In other embodiments, the struts 806a, 806b may be formed by removing material from the body 802 using, for example, laser cutting and/or other material removing procedures.

The apertures 810 may be spread across various portions of the body 802. In the present embodiment, the apertures 810 may be distributed over a distal portion 812, an intermediate portion 814, and/or a proximal portion 816. The size and/or number of apertures 810 may vary between the various portions 812, 814, 816 and may be selected to inhibit passage of and/or to lyse particulates of a selected size while allowing blood components smaller than the selected size to pass through said apertures. For example, in the present embodiment, the distal portion 812 may include generally larger and/or fewer apertures 810 than the intermediate portion 814 and/or the proximal portion 816, the intermediate portion 814 may include generally larger and/or fewer apertures 810 than the proximal portion 816, and/or the proximal portion 816 may include generally smaller and/or more apertures 810 than the intermediate portion 814 and/or the distal portion 812. Such a configuration may capture and/or lyse a variety of particles. In other embodiments, the apertures 810 may be distributed over more and/or fewer portions.

The body 802 may include an engaging portion 820 that may be configured to engage an inner surface of the body lumen. In the present embodiment, the engaging portion 820 may include a tissue engaging portion (not shown) that may include a portion, such as the proximal portion 816 of the outer surface 804. The tissue engaging portion may engage the tissue on the inner surface of the body lumen. The surface area of the tissue engaging portion, in the present embodiment, may be determined to facilitate engagement of the inner wall of the body lumen.

In addition, the implantable lumen filter 800 may include one or more elements or components of the implantable lumen filters 1100, 1200, 1300, 1400, 1500, 1700, 1900,

2000 illustrated in FIGS. 11-20 and described in more detail below. In further embodiments, the implantable lumen filter 800 may include the engagement portion 920 and/or retrieval portion 1030 illustrated in FIGS. 9-10, respectively, and described in more detail below.

Figure 9A:
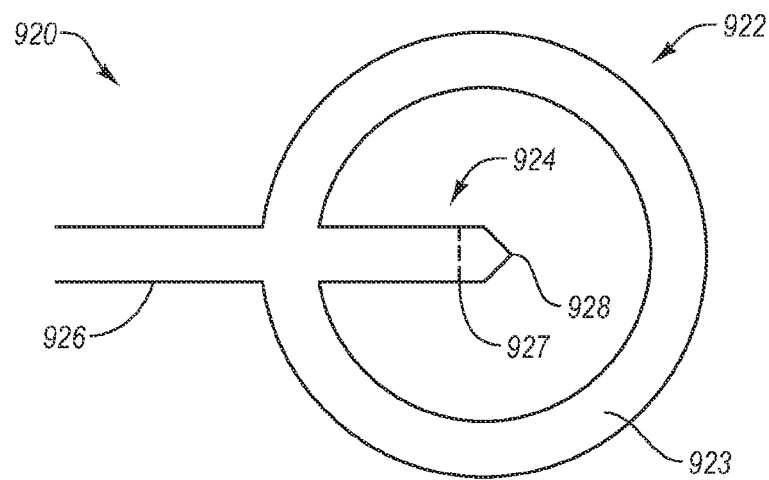
FIGS. 9A-9B illustrate an embodiment of an engagement portion.
Figure 9B:
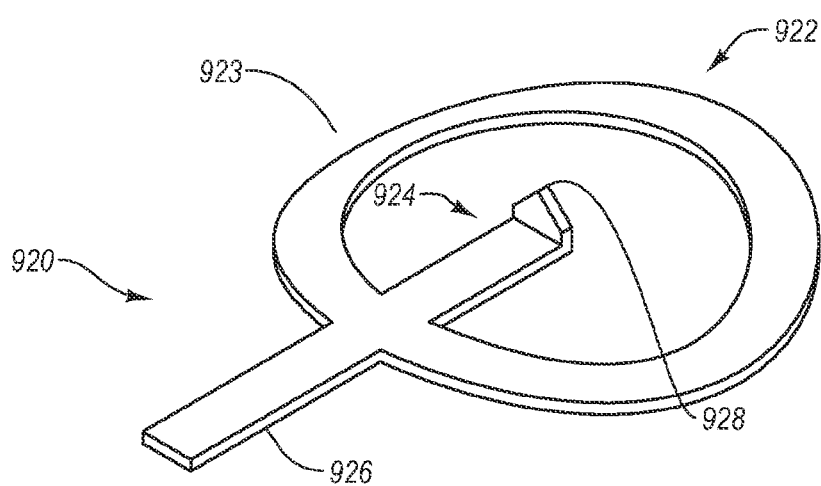

FIGS. 9A-9B illustrate an embodiment of an engaging portion 920. The engaging portion 920 of this embodiment may be functionally similar to the engagement portions 120, 220, 320, 420, 520, 620, 720, 820 previously described above and shown in FIGS. 1-8 in most respects, wherein certain features will not be described in relation to this embodiment wherein those components may function in the manner as described above and are hereby incorporated into this alternative embodiment described below. Like structures and/or components may be given like reference numerals.

The engaging portion 920 may include a tissue engaging portion 922 and/or a tissue piercing portion 924. The tissue engaging portion 922 may include an outer surface 923 configured to engage an inner surface of a body lumen. In the present embodiment, the tissue engaging portion 922 may form a generally elliptical shape. In other embodiments, the tissue engaging portion 922 may form other shapes such as, a generally polygonal shape and/or other shapes. The shape, size, and/or other features of the engaging portion 920 and/or components thereof may be selected to generally limit motion of the implantable lumen filter within a body lumen.

The tissue piercing portion 924 may include a base portion 926 and/or a piercing portion 928 and may be configured to pierce at least a portion of an inner surface of a body lumen. The tissue piercing portion 924 may be connected to the tissue engaging portion 922. For example, the base portion 926 may be connected to the tissue engaging portion 922. The tissue piercing portion 924 may include a bend and/or score line 927 between the base portion 926 and the piercing portion 928. This line 927 may be used in embodiments where the engaging portion 920 is formed from a single piece of material.

For example, the engaging portion 920 may be initially formed of the same material as a strut (shown, for example, as 706, 806 in FIGS. 7-8), such as nickel titanium or alloys thereof. The tissue engaging portion 922 and/or the tissue piercing portion 924 may be formed from material that forms the engaging portion 920. For example, the tissue engaging portion 922 and/or the tissue piercing portion 924 may be laser cut from the same material. The piercing portion 928 may initially be aligned with the base portion 926. The piercing portion 928 may then be plastically deformed out of a plane formed by the tissue piercing portion 924. The deformation of the piercing portion 928 may be facilitated by the bend and/or score line 927. In other embodiments, the piercing portion 928 may simply be formed in an out of plane orientation.

The engaging portion 920 may be dimensioned, oriented, and/or located with respect to a body (such as body 702, 802 shown in FIGS. 7-8) of an implantable lumen filter. For example, as shown in FIG. 9B, the outer surface 923 of the tissue engaging portion 922 may be curved generally consistent with an inner surface of a body lumen. In another example, the engaging portion 920 may be connected to a strut (such as strut 706, 806 shown in FIGS. 7-8) such that the outer surface 923 of the tissue engaging portion 922 may generally engage an inner surface of a body lumen.

In some embodiments, the use of both a tissue engaging portion 922 and a tissue piercing portion 924 may increase the likelihood that the movement of an engaged implantable lumen filter may be limited.

Figure 10A:
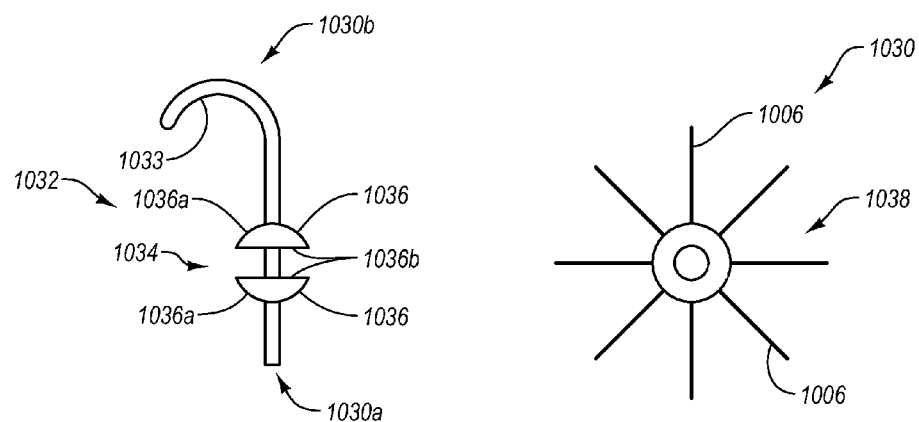
FIGS. 10A-10B illustrate an embodiment of a retrieval portion.
Figure 10B:
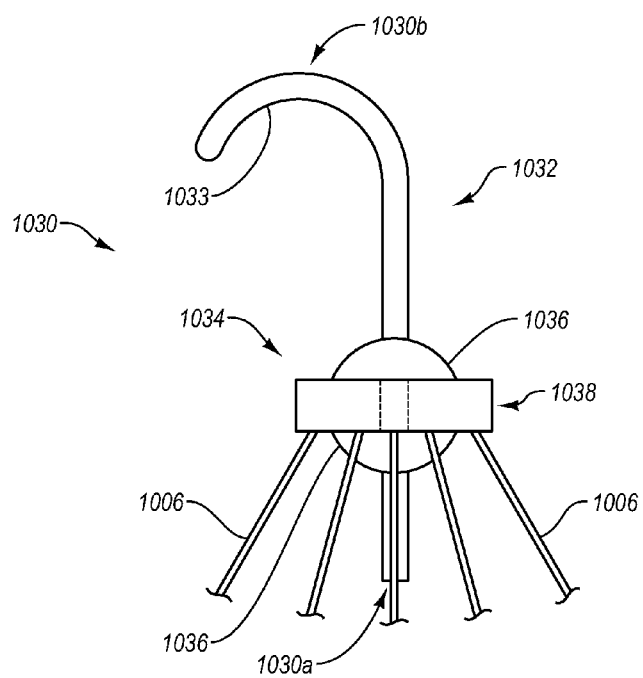

FIGS. 10A-10B illustrate an embodiment of a retrieval portion 1030. The retrieval portion 1030 may be configured to facilitate retrieval of an implantable lumen filter from a deployment site within a body lumen. The retrieval portion 1030 may include a proximal end 1030a, a distal end 1030b, a receiving portion 1032, and/or a connecting portion 1038. The receiving portion 1032 may include a retrieval surface 1033 configured to engage a retrieval member (not shown). The retrieval surface 1033 may be substantially flat, substantially curved, and/or otherwise shaped.

The receiving portion 1032 may include a retaining portion 1034 that may be configured to receive the connecting portion 1038. The retaining portion 1034 may be configured to limit the movement of the connecting portion 1038 with respect to the receiving portion 1032. At least one expanded portion 1036 may be used to limit the movement of the connecting portion 1038 with respect to the receiving portion 1032. The expanded portions 1036 may include slide surface 1036a and/or a stop surface 1036b. The slide surface 1036a, may be ramped, and/or otherwise shaped to allow the connecting portion 1038 to transition over to expanded portions 1036. The stop surface 1036b may be oriented to limit the movement of the connecting portion 1038.

The connecting portion 1038 may be connected to a plurality of struts 1006. In some embodiments, the struts 1006 may be connected to the struts of a corresponding implantable lumen filter, such as, for example, to 706, 806a, 806b near the proximal end 702a, 802a of the implantable lumen filters 700, 800 shown in FIGS. 7-8. In other embodiments, the connecting portion 1038 may be connected to the struts 706, 806a, 806b near the distal end 702b, 802b of the implantable lumen filters 700, 800. With the connecting portion 1038 connected to the plurality of struts 1006, the receiving portion 1032 and the connecting portion 1038 may be engaged.

Figure 11:
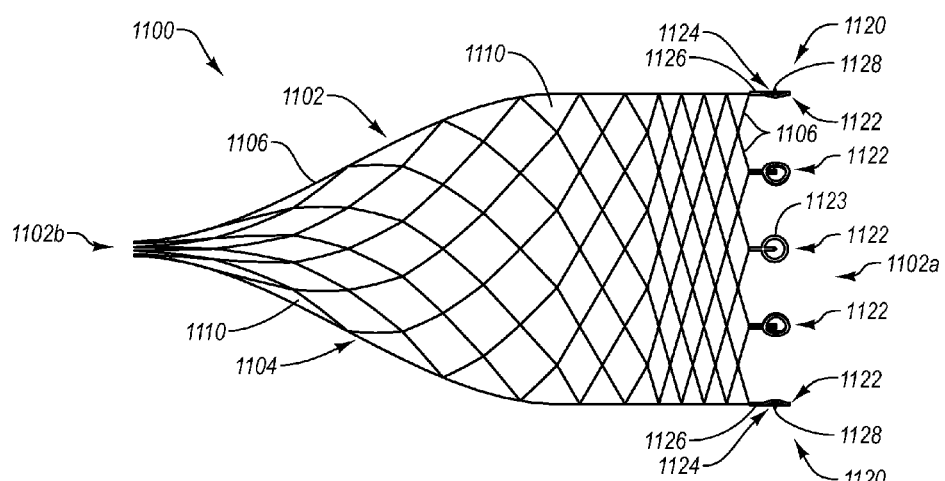
FIG. 11 illustrates another embodiment of the implantable lumen filter of FIG. 7 with an embodiment of an engagement portion.

FIG. 11 illustrates another embodiment of an implantable lumen filter 1100 of with an embodiment of an engagement portion 1120. The implantable lumen filter 1100 and engagement portion 1120 of this other embodiment may be functionally similar to the implantable lumen filters 100, 200, 300, 400, 500, 600, 700, 800 and engagement portions 120, 220, 320, 420, 520, 620, 720, 820, 920 previously described above and shown in FIGS. 1-9 in most respects, wherein certain features will not be described in relation to this embodiment wherein those components may function in the manner as described above and are hereby incorporated into this alternative embodiment described below. Like structures and/or components may be given like reference numerals.

The implantable lumen filter 1100 may include a body 1102 having a proximal end 1102a, a distal end 1102b, and an engagement member 1120. The body 1102 may be transitionable from a compressed state to an expanded state and is shown in the FIG. 11 in the expanded state.

The body 1102 may define an outer surface 1104 that may be defined by a plurality of struts 1106. The struts 1106 may be formed from various materials including nickel titanium and/or alloys thereof. The outer surface 1104, in the present embodiment, may have a generally concave conic shape from a base near the proximal and 1102a toward an apex at the distal and 1102b. In other embodiments, the outer surface 1104 may have other shapes.

The struts 1106 may form a plurality of apertures 1110. In the embodiment illustrated in FIG. 11, the struts 1106 form generally diamond shaped apertures 1110. The apertures 1110 may be spread across various portions of the body 1102. The struts 1106 may be welded or otherwise connected together. In other embodiments, the struts 1106 may be formed by removing material from the body 1102 using, for example, laser cutting and/or other material removing procedures. The apertures 1110 may be spread across various portions of the body 1102. In the present embodiment, the apertures 1110 may be distributed over various portions having varying number and/or aperture size. In other embodiments, the apertures 1110 may be uniformly and/or otherwise distributed.

The body 1102 may include an engaging portion 1120 that may be configured to engage an inner surface of a body lumen. The engaging portion 1120 may include a tissue engaging portion 1122 and/or a tissue piercing portion 1124. The tissue engaging portion 1122 may include an outer surface 1123 configured to engage an inner surface of a body lumen. The tissue engaging portion 1122 may form a generally elliptical shape. The shape, size, and/or other features of the engaging portion 1120 and/or components thereof may be selected to generally limit motion of the implantable lumen filter 1100 within a body lumen.

The tissue piercing portion 1124 may include a base portion 1126 and/or a piercing portion 1128 and may be configured to pierce at least a portion of an inner surface of a body lumen. The tissue piercing portion 1124 may be connected to the tissue engaging portion 1122. For example, the base portion 1126 may be connected to the tissue engaging portion 1122. The tissue piercing portion 1124 may include at least one bend and/or score line (shown as 927 in FIG. 9A) between the base portion 1126 and the piercing portion 1128.

The engaging portion 1120 may be dimensioned, oriented, and/or located with respect to the body 1102 of the implantable lumen filter 1100. For example, the outer surface (shown as 923 in FIGS. 9A-9B) of the tissue engaging portion 1122 may be generally curved consistent with an inner surface of a body lumen. In another example, the engaging portion 1120 may be connected to an extending strut 1106a such that the outer surface of the tissue engaging portion 1122 may generally engage an inner surface of a body lumen.

In some embodiments, the use of both a tissue engaging portion 1122 and a tissue piercing portion 1124 may increase the likelihood that the movement of an engaged implantable lumen filter 1100 may be limited.

In addition, the implantable lumen filter 1100 may include one or more elements or components of the implantable lumen filters 1200, 1300, 1400, 1500, 1700, 1900, 2000 illustrated in FIGS. 12-20 and described in more detail below.

Figure 12:
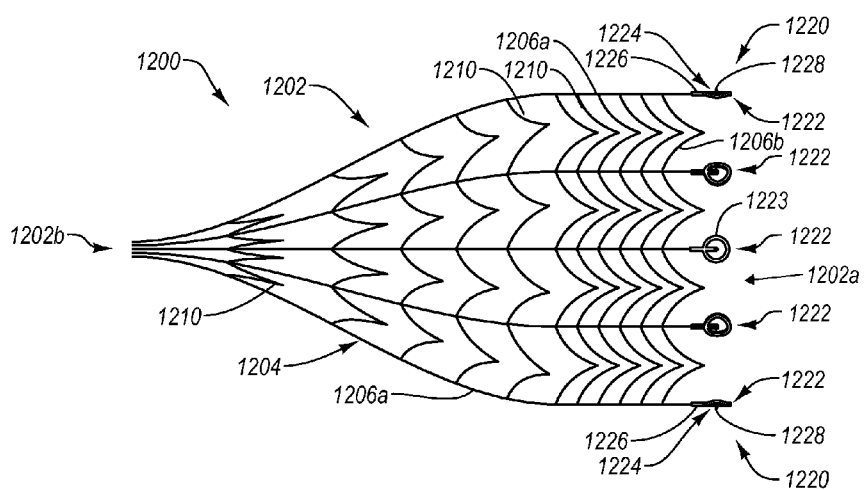
FIG. 12 illustrates another embodiment of the implantable lumen filter of the FIG. 8 with an embodiment of an engagement portion.

FIG. 12 illustrates another embodiment of the implantable lumen filter 1200 with an embodiment of an engagement portion 1220. The implantable lumen filter 1200 and engagement portion 1220 of this other embodiment may be functionally similar to the implantable lumen filters 100, 200, 300, 400, 500, 600, 700, 800, 1100 and engagement portions 120, 220, 320, 420, 520, 620, 720, 820, 920, 1120 previously described above and shown in FIGS. 1-9 and 11 in most respects, wherein certain features will not be described in relation to this embodiment wherein those components may function in the manner as described above and are hereby incorporated into this alternative embodiment described below. Like structures and/or components are given like reference numerals.

The implantable lumen filter 1200 may include a body 1202 having a proximal end 1202a, a distal end 1202b, and an engagement member 1220. The body 1202 may be transitionable from a compressed state to an expanded state and is shown in the FIG. 12 in the expanded state.

The body 1202 may define an outer surface 1204 that may be defined by a plurality of struts 1206a, 1206b. In the present embodiment, some of the struts 1206a extend from the distal end 1202b toward the proximal and 1202a and some struts 1206b may intersect the extending struts 1206a.

The struts 1206a, 1206b may be formed from various materials including nickel titanium and/or alloys thereof. The outer surface 1204, in the present embodiment, may have a generally concave conic shape from a base near the proximal and 1202a toward an apex at the distal and 1202b. In other embodiments, the outer surface 1204 may have other shapes.

The struts 1206a, 1206b may form a plurality of apertures 1210. In the embodiment illustrated in FIG. 12, the struts 1206a, 1206b form generally chevron shaped apertures 1210. For example, a pair of intersecting struts 1206b may form a "V"-shaped web between two extending struts 1206a. The struts 1206a, 1206b may form other shapes. In the present embodiment, the struts 1206a, 1206b may be welded and/or otherwise connected together. For example, the extending struts 1206a may be welded together near the distal end 1202b while the intersecting struts 1206b may be welded to the extending struts 1206b. In other embodiments, the struts 1206a, 1206b may be formed by removing material from the body 1202 using, for example, laser cutting and/or other material removing procedures. The apertures 1210 may be spread across various portions of the body 1202. In the present embodiment, the apertures 1210 may be distributed over various portions having varying number and/or aperture size. In other embodiments, the apertures 1210 may be uniformly and/or otherwise distributed.

The body 1202 may include an engaging portion 1220 that may be configured to engage an inner surface of a body lumen. The engaging portion 1220 may include a tissue engaging portion 1222 and/or a tissue piercing portion 1224. The tissue engaging portion 1222 may include an outer surface 1223 configured to engage an inner surface of a body lumen. In the present embodiment, the tissue engaging portion 1222 may form a generally elliptical shape. The shape, size, and/or other features of the engaging portion 1220 and/or components thereof may be selected to generally limit motion of the implantable lumen filter 1200 within a body lumen.

The tissue piercing portion 1224 may include a base portion 1226 and/or a piercing portion 1228 and may be configured to pierce at least a portion of an inner surface of a body lumen. The tissue piercing portion 1224 may be connected to the tissue engaging portion 1222. For example, the base portion 1226 may be connected to the tissue engaging portion 1222. The tissue piercing portion 1224 may include a bend and/or score line (shown as 927 in FIG. 9A) between the base portion 1226 and the piercing portion 1228.

The engaging portion 1220 may be dimensioned, oriented, and/or located with respect to the body 1202 of the implantable lumen filter 1200. For example, the outer surface (shown as 923 in FIGS. 9A-9B) of the tissue engaging portion 1222 may be generally curved consistent with an inner surface of a body lumen. In another example, the engaging portion 1220 may be connected to an extending strut 1206a such that the outer surface of the tissue engaging portion 1222 may generally engage an inner surface of a body lumen.

In some embodiments, the use of both a tissue engaging portion 1222 and a tissue piercing portion 1224 may increase the likelihood that the movement of an engaged implantable lumen filter may be limited.

In addition, the implantable lumen filter 1200 may include one or more elements or components of the implantable lumen filters 1300, 1400, 1500, 1700, 1900, 2000 illustrated in FIGS. 13-20 and described in more detail below.

Figure 13:
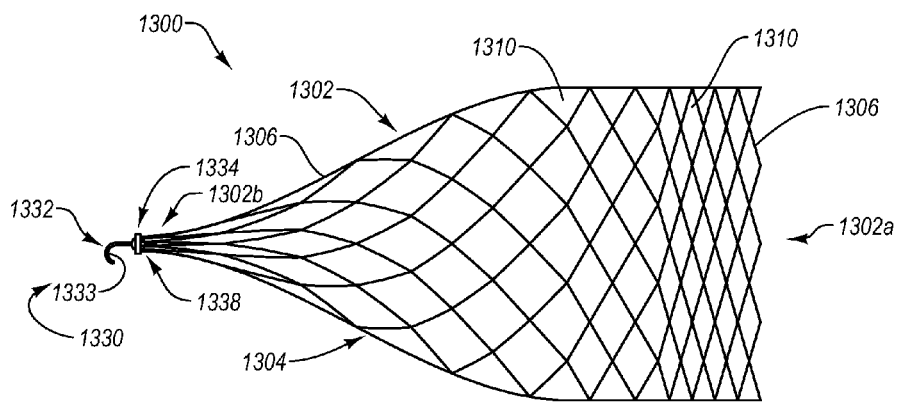
FIG. 13 illustrates a further embodiment of the implantable lumen filter of FIG. 7 with an embodiment of a retrieval portion.

FIG. 13 illustrates a further embodiment of the implantable lumen filter 1300 with an embodiment of a retrieval portion 1330. The implantable lumen filter 1300 and retrieval portion 1330 of this other embodiment may be functionally similar to the implantable lumen filters 100, 200, 300, 400, 500, 600, 700, 800, 1100, 1200 and retrieval portion 1030 previously described above and shown in FIGS. 1-8 and 10-12 in most respects, wherein certain features will not be described in relation to this embodiment wherein those components may function in the manner as described above and are hereby incorporated into this alternative embodiment described below. Like structures and/or components may be given like reference numerals.

The implantable lumen filter 1300 may include a body 1302 having a proximal end 1302a, a distal end 1302b, and a retrieval portion 1330. The body 1302 may be transitionable from a compressed state to an expanded state and is shown in the FIG. 13 in the expanded state.

The body 1302 may define an outer surface 1304 that may be defined by a plurality of struts 1306. The struts 1306 may be formed from various materials including nickel titanium and/or alloys thereof. The outer surface 1304, in the present embodiment, may have a generally concave conic shape from a base near the proximal and 1302a toward an apex at the distal and 1302b. In other embodiments, the outer surface 1304 may be otherwise shaped.

The struts 1306 may form a plurality of apertures 1310. In the embodiment illustrated in FIG. 13, the struts 1306 form generally diamond shaped apertures 1310. The apertures 1310 may be spread across various portions of the body 1302. The struts 1306 may be welded or otherwise connected together. In other embodiments, the struts 1306 may be formed by removing material from the body 1302 using, for example, laser cutting and/or other material removing procedures. The apertures 1310 may be spread across various portions of the body 1302.

In the present embodiment, the apertures 1310 may be distributed over various portions having varying number and/or aperture size. In other embodiments, the apertures 1310 may be uniformly and/or otherwise distributed.

The body 1302 may include a retrieval portion 1330 that may be configured to facilitate retrieval of the implantable lumen filter 1300 from a deployment site within a body lumen. The retrieval portion 1330 may include a proximal end, a distal end (shown as 1030a and 1030b, respectively, in FIGS. 10A-10B), a receiving portion 1332, and/or a connecting portion 1338. The receiving portion 1332 may include a retrieval surface 1333 configured to engage a retrieval member (not shown). The retrieval surface 1333 may be substantially flat, substantially curved, and/or otherwise shaped.

The receiving portion 1332 may include a retaining portion 1334 that may be configured to receive the connecting portion 1338. The retaining portion 1334 may be configured to limit the movement of the connecting portion 1338 with respect to the receiving portion 1332. At least one expanded portion (shown as 1036 in FIGS. 10A-10B) may be used to limit the movement of the connecting portion 1338 with respect to the receiving portion 1332.

The connecting portion 1338 may be connected to the plurality of struts 1306. With the connecting portion 1338 committed to the plurality of struts 1306, the receiving portion 1332 and the connecting portion 1338 may be engaged.

In addition, the implantable lumen filter 1300 may include one or more elements or components of the implantable lumen filters 1400, 1500, 1700, 1900, 2000 illustrated in FIGS. 14-20 and described in more detail below.

Figure 14:
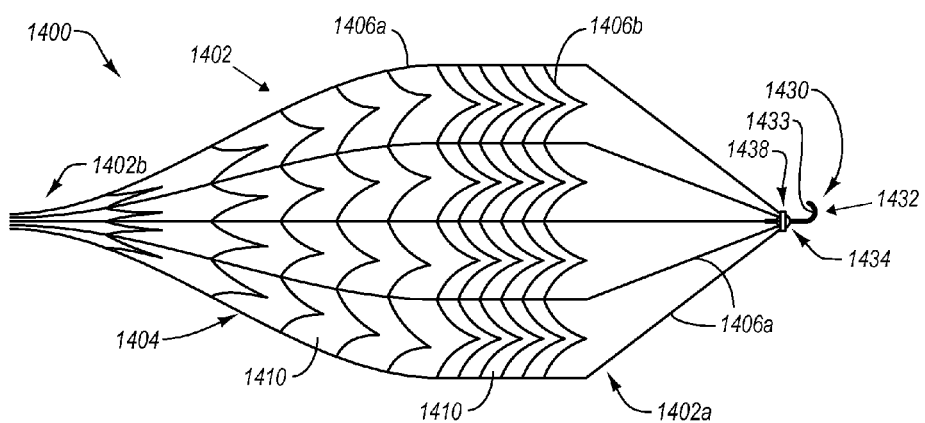
FIG. 14 illustrates a further embodiment of the implantable lumen filter of FIG. 8 with an embodiment of a retrieval portion.

FIG. 14 illustrates a further embodiment of the implantable lumen filter 1400 with an embodiment of a retrieval portion 1430. The implantable lumen filter 1400 and retrieval portion 1430 of this other embodiment may be functionally similar to the implantable lumen filters 100, 200, 300, 400, 500, 600, 700, 800, 1100, 1200, 1300 and retrieval portions 1030, 1330 previously described above and shown in FIGS. 1-8 and 10-13 in most respects, wherein certain features will not be described in relation to this embodiment wherein those components may function in the manner as described above and are hereby incorporated into this alternative embodiment described below. Like structures and/or components may be given like reference numerals.

The implantable lumen filter 1400 may include a body 1402 having a proximal end 1402a, a distal end 1402b, and a retrieval portion 1430. The body 1402 may be transitionable from a compressed state to an expanded state and is shown in the FIG. 14 in the expanded state.

The body 1402 may define an outer surface 1404 that may be defined by a plurality of struts 1406a, 1406b. In the present embodiment, some of the struts 1406a extend from the distal end 1402b toward the proximal and 1402a and some struts 1406b may intersect the extending struts 1406a. The struts 1406a, 1406b may be formed from various materials including nickel titanium and/or alloys thereof. The outer surface 1404, in the present embodiment, may have a generally concave conic shape from a base near the proximal and 1402a toward an apex at the distal and 1402b. In other embodiments, the outer surface 1404 may be otherwise shaped.

The struts 1406a, 1406b may form a plurality of apertures 1410. In the embodiment illustrated in FIG. 14, the struts 1406a, 1406b form generally chevron shaped apertures 1410. For example, a pair of intersecting struts 1406b may form a "V"-shaped web between two extending struts 1406a. The struts 1406a, 1406b may form other shapes. In the present embodiment, the struts 1406a, 1406b may be welded and/or otherwise connected together. For example, the extending struts 1406a may be welded together near the distal end 1402b while the intersecting struts 1406b may be welded to the extending struts 1406b. In other embodiments, the struts 1406a, 1406b may be formed by removing material from the body 1402 using, for example, laser cutting and/or other material removing procedures.

The apertures 1410 may be spread across various portions of the body 1402. In the present embodiment, the apertures 1410 may be distributed over various portions having varying number and/or aperture size. In other embodiments, the apertures 1410 may be uniformly and/or otherwise distributed.

The body 1402 may include a retrieval portion 1430 that may be configured to facilitate retrieval of the implantable lumen filter 1400 from a deployment site within a body lumen. The retrieval portion 1430 may include a proximal end, a distal end (shown as 1030a and 1030b, respectively in FIGS. 10A-10B), a receiving portion 1432, and/or a connecting portion 1438. The receiving portion 1432 may include a retrieval surface 1433 configured to engage a retrieval member (not shown). The retrieval surface 1433 may be substantially flat, substantially curved, and/or otherwise shaped.

The receiving portion 1432 may include a retaining portion 1434 that may be configured to receive the connecting portion 1438. The retaining portion 1434 may be configured to limit the movement of the connecting portion 1438 with respect to the receiving portion 1432. At least one expanded portion (shown as 1036 in FIGS. 10A-10B) may be used to limit the movement of the connecting portion 1438 with respect to the receiving portion 1432.

The connecting portion 1438 may be connected to at least one of the extending struts 1406a. In other embodiments, the connecting portion 1438 may be connected to at least one extending strut 1406a, at least one intersecting strut 1406b, and/or combinations thereof. With the connecting portion 1438 committed to at least one strut 1406a, 1406b, the receiving portion 1432 and the connecting portion 1438 may be engaged.

In addition, the implantable lumen filter 1400 may include one or more elements or components of the implantable lumen filters 1500, 1700, 1900, 2000 illustrated in FIGS. 15-20 and described in more detail below.

Figures 15A, 15C:
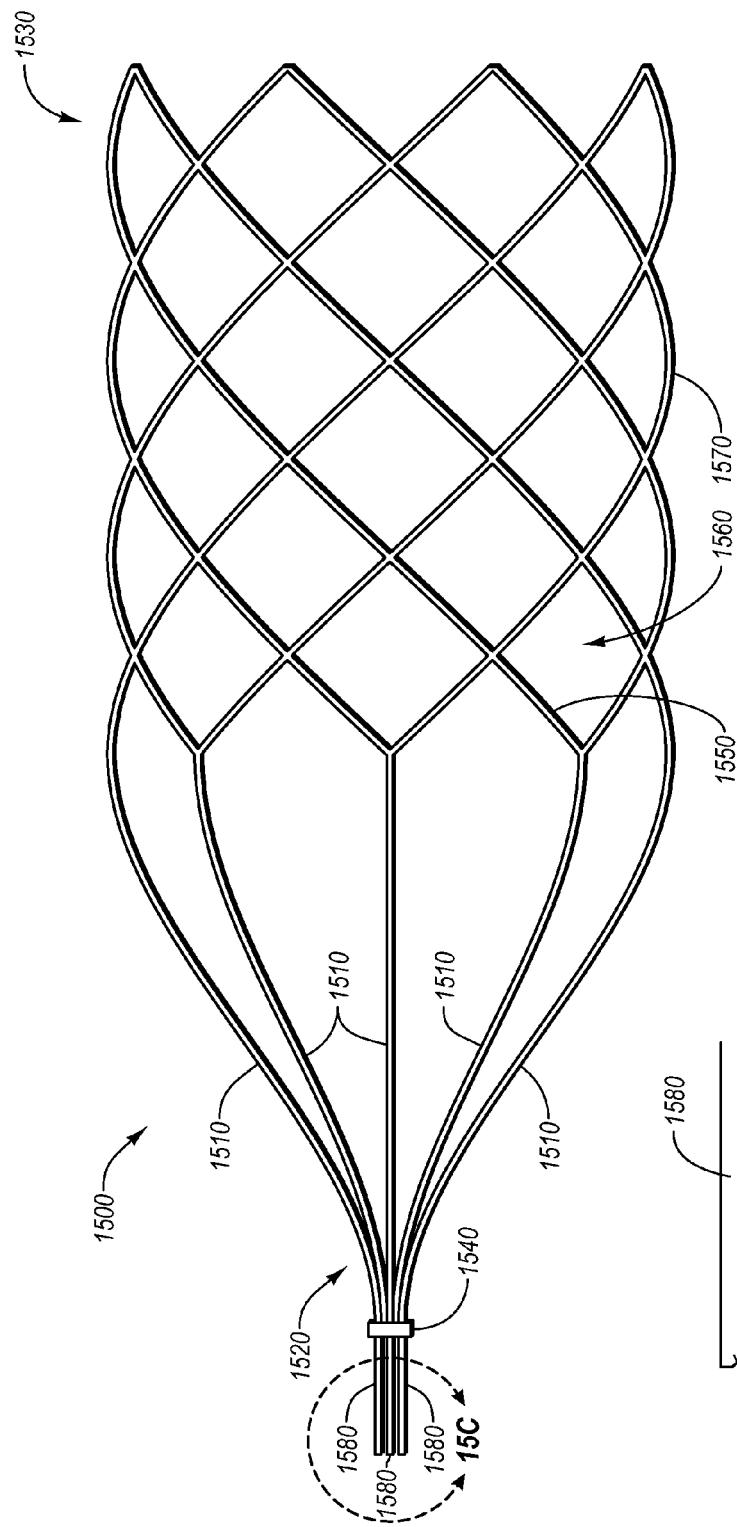
FIG. 15A illustrates an embodiment of an implantable lumen filter in a deployed state.
FIG. 15C illustrates a proximal end of an example implantable lumen filter.
Figure 15B:
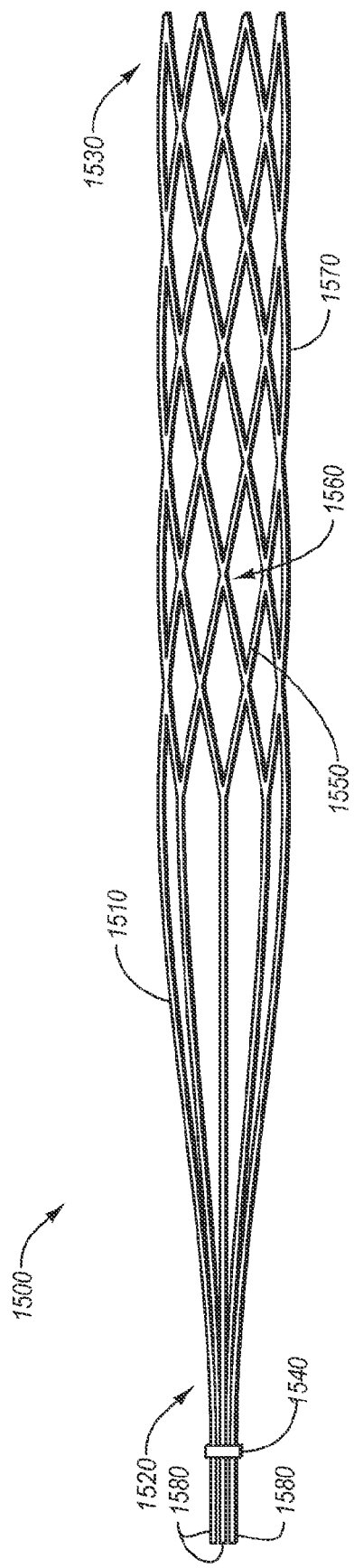
FIG. 15B illustrates an additional embodiment of an implantable lumen filter in a pre-deployed state.

FIGS. 15A-15C illustrate a further embodiment of the implantable lumen filter 1500. The implantable lumen filter 1500 of this embodiment may be functionally similar to the implantable lumen filters 100, 200, 300, 400, 500, 600, 700, 800, 1100, 1200, 1300, 1400 previously described above and shown in FIGS. 1-8 and 10-14 in most respects, wherein certain features will not be described in relation to this embodiment wherein those components may function in the manner as described above and are hereby incorporated into this alternative embodiment described below. Like structures and/or components may be given like reference numerals.

In FIG. 15A the body lumen filter 1500 is shown in a deployed state. The body lumen filter 1500 includes primary struts 1510 that extend between a proximal or first end 1520 and a distal or second end 1530. The primary struts 1510 can be coupled together near a first end 1520 by a ring 1540. Accordingly, near the ring 1540 the primary struts 1510 can be relatively close together. As the primary struts 1510 extend away from the ring 1540 toward the second end 1530, the primary struts 1510 begin to separate in a radial direction.

The body lumen filter 1500 further includes additional structures, such as secondary struts 1550 that interact with other primary struts 1510 and other secondary struts 1550 to form a filter body having filtering openings 1560 defined therein. Further, the distribution of the primary struts 1510 and the secondary struts 1550 are distributed about a perimeter of the body lumen filter 1500 at various locations between the first end 1520 and the second 1530.

The configuration of the primary struts 1510 and the secondary struts 1550 can form arcuate anchors 1570. The arcuate anchors 1570 can be distributed about a periphery of the body lumen filter 1500 between the first end 1520 and the second end 1530. Further, the arcuate anchors 1570 can be located at multiple axial locations between the first end 1520 and the second 1530, such as being arranged in multiple rows as illustrated in FIG. 15A.

In addition, the arcuate anchors 1570 can be configured to be relatively stiff. As a result, as the body lumen filter 1500 moves toward the deployed state illustrated in FIG. 15A, the body lumen filter 1500 can exert a relatively large radial force. Further, the relative stiffness of the primary struts 1510 may allow the body lumen filter 1500 to include a relatively low number of primary struts 1510. Various numbers of primary struts 1510 can be included in the body lumen filter. For example, in one configuration eight primary struts can be included. It will be understood, however, that a lesser or greater number of struts is also possible. Such a configuration can help improve efficient blood flow through the body lumen filter 1500 when the body lumen filter 1500 is deployed by helping align the flow while reducing disturbances of the blood as it flows into contact with the body lumen filter 1500.

Further, the arcuate anchor 1570 can evenly distribute the relatively large radial forces to a body vessel in which the body lumen filter 1500 is deployed such that the arcuate anchors 1570 act to secure the body lumen filter 1500 to the body vessel. Such a configuration can help maintain the body lumen filter at the intended location while reducing or eliminating the possibility that the arcuate anchor 1570 will pierce an intima layer of the body lumen.

As illustrated in FIG. 15A, the arcuate anchor 1570 can have radii of curvature to aid with engaging the filter within the body lumen. While the arcuate anchors 1570 shown have similar radii or curvature, it will be appreciated that arcuate anchor 1570 can have different radii of curvature as desired.

The body lumen filter 1500 can be formed in any manner. In at least one example, the primary struts 1510 and secondary struts 1550 can be formed first, such as by etching, cutting, rolling, or any combination of processes. The arcuate anchors 1570 can be integrally formed during the formation of the primary struts and/or the secondary struts or they can be formed afterward.

With continued reference to FIG. 15A, extending proximally from the ring 1540 are one or more members 1580. These one or more members 1580 can be formed from a proximal portion of one or more of the primary struts 1510 or alternatively be separate members connected or coupled to the ring 1540. In the illustrated configuration, four members 1580 are illustrated although a number of members lesser or greater than four are possible. The members 1580 can be configured to aid with capturing and optionally deployment of the body lumen filter 1500. In one configuration, as shown in FIG. 15C for example, one or more of the members 1580 include a capture structure 1590 to facilitate capturing of the body lumen filter 1500 following deployment. The capture structure 1590 can be a hook or other extension from the member 1580 which may be hooked or otherwise engaged, and has sufficient strength and rigidity, to allow controlled movement of the body lumen filter 1500 during retrieval. It will be understood that the same capture structure 1590, or modified capture structure, can be used to deliver or deploy the body lumen filter.

In addition, the implantable lumen filter 1500 may include one or more elements or components of the implantable lumen filters 1700, 1900, 2000 illustrated in FIGS. 17-20 and described in more detail below.

Figure 16A:
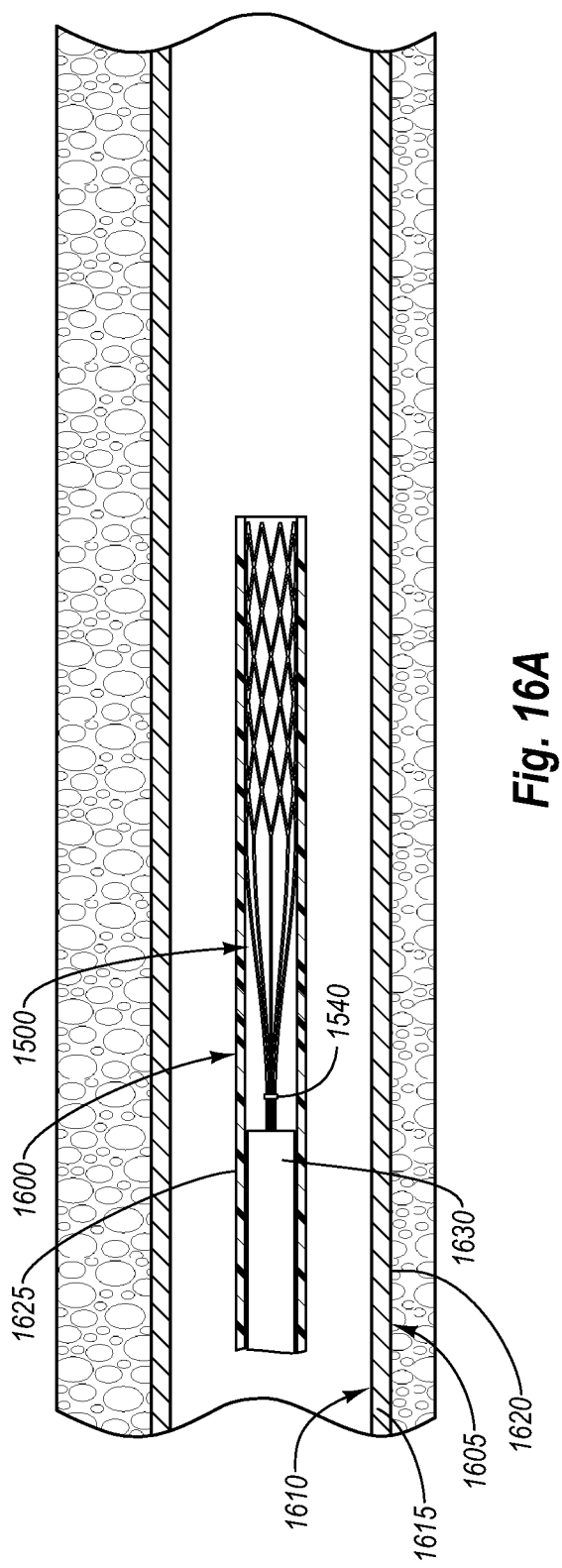
FIG. 16A illustrates an embodiment of an implantable lumen filter in a pre-deployed state being introduced into a body lumen by a deployment device.

FIG. 16A illustrates the body lumen filter 1500 in a pre-deployed configuration and located within a deployment device 1600. The deployment device 1600 is configured to deploy the filter 1500 into a body lumen 1605. The body lumen 1605 includes an inner layer or intima layer 1610, a medial layer 1615, and an adventitial layer 1620. The deployment device 1600 can include a housing 1625 and a delivery mechanism 1630 that is actuated from a proximally located handle (not shown).

Figure 16B:
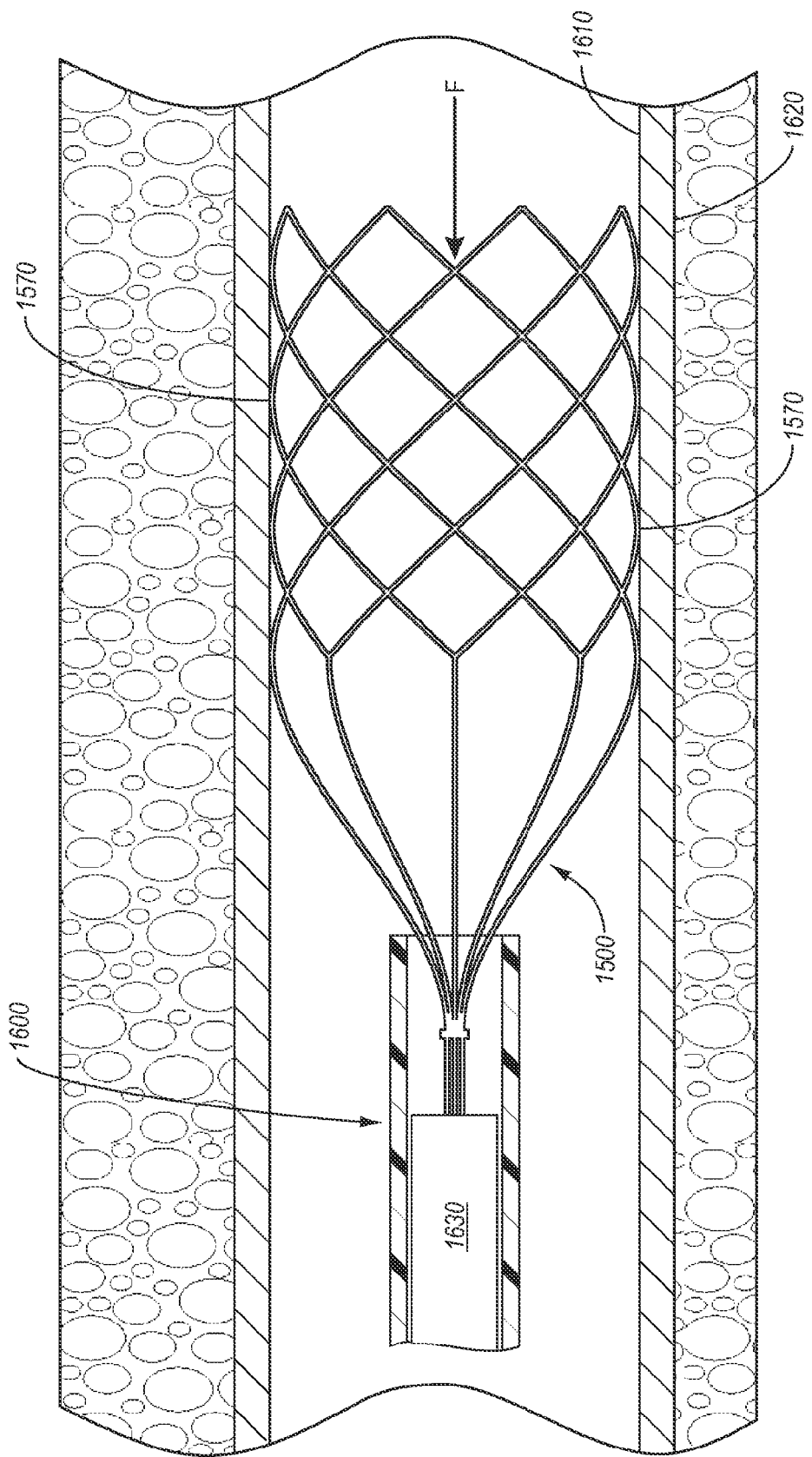
FIG. 16B illustrates an embodiment of an implantable lumen filter in a deployed state in a body lumen.

As previously discussed, the body lumen filter 1500 includes primary struts 1510 and secondary struts 1550 that are interconnected in such a manner as to allow the body lumen filter 1500 to be moved from the pre-deployed state illustrated in FIG. 16A to a deployed state illustrated in FIG. 16B. Further, the primary struts 1510 and secondary struts 1550 are formed and interconnected such that the arcuate anchors 1570 are distributed about at least a portion of the perimeter of the body lumen filter 1500 in the deployed state.

To deploy the body lumen filter 1500, the deployment device 1600 is moved to a desired location within a body lumen 1605 by using a catheter or other well-known techniques. In at least one example, the ring 1540 can be made of a radiopaque material, coated with a radiopaque material, and/or include one or more recesses, apertures, or holes that can receive a radiopaque marker or material. Such a configuration can allow a practitioner to view the location of the body lumen filter 1500 as it moves to the desired location. In another example, the deployment device 1600 may be advanced to the desired location, the delivery mechanism 1630 may be advanced distally to abut the body lumen filter 1500, the housing 1625 may be retracted to deploy the body lumen filter 1500, or combinations thereof.

As the body lumen filter 1500 is deployed by the deployment device 1600, the body lumen filter 1500 may move toward the deployed state. For instance, for a body lumen filter 1500 formed from a shape memory material, moving the delivery mechanism 1630 distally, moving the housing 1625 proximally, or a combination of such movements, may release the body lumen filter 1500 from within the housing 1625 to transition to the deployed state of FIG. 16B.

As the body lumen filter 1500 is advanced from housing 1625, the body lumen filter 1500 is moved towards the deployed state. For instance, when the body lumen filter 1500 is formed from a shape memory material, such that, moving the delivery mechanism 1630 distally, moving the housing 1625 proximally, or a combination of such movements, releases the body lumen filter 1500 from within the housing 1625 to transition to the deployed state of FIG. 16B.

Embodiments of the endoprosthesis body can include a material made from any of a variety of known suitable materials, such as a shaped memory material (SMM). For example, the SMM can be shaped in a manner that allows for restriction to induce a substantially tubular, linear orientation while within a delivery shaft, but can automatically retain the memory shape of the endoprosthesis once extended from the delivery shaft. SMMs have a shape memory effect in which they can be made to remember a particular shape. Once a shape has been remembered, the SMM can be bent out of shape or deformed and then returned to its original shape by unloading it from strain or heating. Typically, SMMs can be shape memory alloys (SMA) comprised of metal alloys, or shape memory plastics (SMP) comprised of polymers. The materials can also be referred to as being superelastic.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as nitinol; and cobalt-chromium-nickel alloys; nickel-titanium platinum; nickel-titanium palladium or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture.

For example, the primary material of an endoprosthesis can be of a NiTi alloy that forms superelastic nitinol. In the present case, nitinol materials can be trained to remember a certain shape, straightened in a shaft, catheter, or other tube, and then released from the catheter or tube to return to its trained shape. Also, additional materials can be added to the nitinol depending on the desired characteristic. The alloy can be utilized having linear elastic properties or non-linear elastic properties.

An SMP is a shape-shifting plastic that can be fashioned into an endoprosthesis in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of an endoprosthesis by heating it above the Ttr, fixing the SMP into the new shape, and cooling the material below Ttr. The SMP can then be arranged into a temporary shape by force and then resume the memory shape once the force has been applied. Examples of SMPs include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

An endoprosthesis body having at least one layer made of an SMM or suitable superelastic material and other suitable layers can be compressed or restrained in its delivery configuration within a delivery device using a sheath or similar restraint, and then deployed to its desired configuration at a deployment site by removal of the restraint as is known in the art. An endoprosthesis body made of a thermally-sensitive material can be deployed by exposure of the endoprosthesis to a sufficient temperature to facilitate expansion as is known in the art. It will be appreciated that the body lumen filter 1500 can be mechanically expanded, such as by a balloon or other expanding device.

Continuing with the example illustrated in FIG. 16B, as the body lumen filter 1500 is moved toward the deployed state, the expandable struts 1510 can be displaced to provide the filter openings 1560. The filter openings 1560 can be sized to prevent particulates, such as an embolus, from passing through the body lumen filter 1500. While the embolus is trapped against body lumen filter 1500, blood will continue to flow over the embolus. The flow of blood over the embolus can dissolve the embolus through the body's lysing process. Additionally, the body lumen filter 1500 may be coated with a beneficial agent that may facilitate lysing of the embolus.

The blood flow F exerts a fluid force on the body lumen filter 1500 that would tend to move the body lumen filter 1500 in the direction of the blood flow F. The arcuate anchors 1570 counter this force to maintain the body lumen filter 1500 at an intended deployment location. In particular, frictional, compressive, and/or other forces between the body lumen filter 1500 and the body lumen 1605 can maintain the body lumen filter 1500 at the intended deployment location, as will now be described in more detail below.

As the vascular device 1500 is moved toward the deployed state, the arcuate anchors 1570 are moved into contact with the intima layer 1610 of the body lumen 1605. In the deployed state, a diametrical distance of the body lumen filter between the arcuate anchors 1570 on opposing sides of the body lumen filter 1510 can be separated by a distance that is slightly larger than the diameter of the body lumen 1605 before the vascular device 1500 is deployed. As a result, a slight tensile force can urge or press the arcuate anchors 1570 into contact with the intima layer 1610.

As the arcuate anchors 1570 are urged into contact with the intima layer 1610, the intima layer 1610 can deform slightly to begin to conform to the shape of the arcuate anchors 1570, which can result in compressive forces between the arcuate anchors 1570 and the body lumen 1605.

Further, this deformation can increase contact between the arcuate anchor 1570 and the intima layer 1610. Frictional forces between two objects that are in contact depend on the normally applied force and the coefficient of friction between the two objects. The normally applied force depends on the area of contact and the pressure applied to that area. The coefficient of friction as well as the normal force necessary to maintain the body lumen filter 1500 positioned in body lumen 1605 may be relatively constant. Accordingly, increasing the surface area over which the arcuate anchor 1570 applies the normal force can reduce the pressure the arcuate anchor 1570 applies to the body lumen 1605. Decreasing the pressure applied to the body lumen 1605 in turn can reduce the possibility that the arcuate anchors 1570 will pierce the intima layer 1610.

Accordingly, the relatively large surface area of the anchors 1540 can help maintain the body lumen filter 1500 at or near a desired deployment location in the body lumen 1605. Further, the relatively large surface area of the anchors 1540 can reduce the likelihood that the anchors 1540 will penetrate through the intima layer 1610 and into the medial layer 1615 and/or the adventitial layer. Reducing penetration into the medial layer 1615 can in turn reduce endothelial growth while the body lumen filter 1500 is deployed. While the embolus is trapped against body lumen filter 1600, blood will continue to flow over the embolus. The flow of blood over the embolus can dissolve the embolus through the body's lysing process. The blood flow F exerts a fluid force on the body lumen filter 1600 that would tend to move the body lumen filter 1600 in the direction of the blood flow F. The arcuate anchors 1570 counter this force to maintain the body lumen filter 1600 in an intended deployment location.

Referring briefly again to FIG. 15B, while described as arcuate anchors 1570 can have other atraumatic shapes, such as elliptically curved. Further, while the arcuate anchors 1570 are also described as expanding radially outward, it will be appreciated that the arcuate anchors 1570 can extend outwardly at an angle. Such a configuration can provide arcuate anchor 1570 that can have smooth edges. Referring again to FIG. 16B, relatively smooth edges can distribute the compressive forces discussed above in a relatively even manner across the arcuate anchor 1570 to thereby reduce the likelihood that the arcuate anchor 1570 will pierce the intima layer 1610. Reducing the penetration of the arcuate anchor 1570 through the intima layer 1610 can in turn reduce endothelial growth, which can reduce trauma associated with retrieval of the body lumen filter 1500 as described above.

Figure 17:
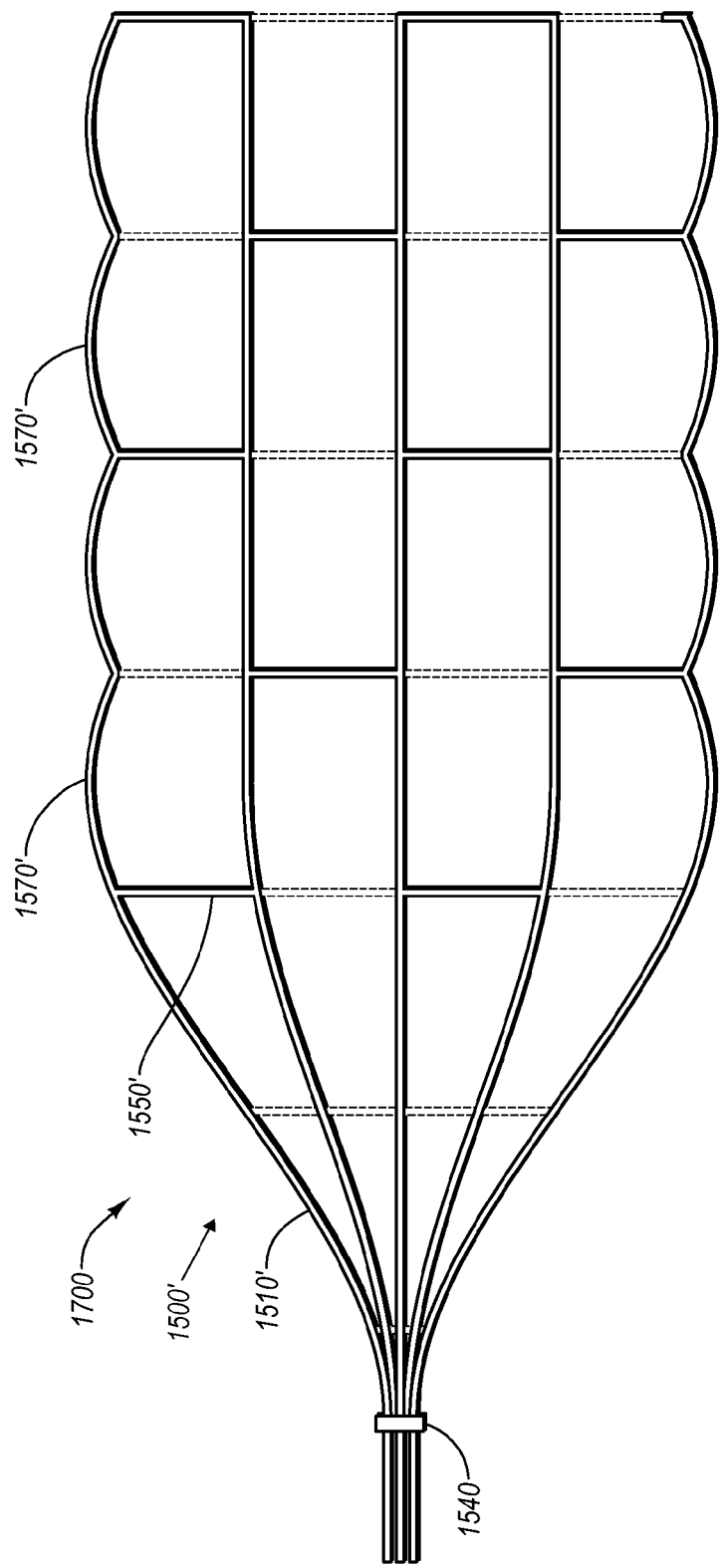
FIG. 17 illustrates a further embodiment of an implantable lumen filter in a deployed state.

Further, in at least one example, a body lumen filter can be provided with a different shape or configuration. For example, FIG. 17 illustrates a further embodiment of the implantable lumen filter 1700. The implantable lumen filter 1700 of this embodiment may be functionally similar to the implantable lumen filters 100, 200, 300, 400, 500, 600, 700, 800, 1100, 1200, 1300, 1400, 1500 previously described above and shown in FIGS. 1-8 and 10-16 in most respects, wherein certain features will not be described in relation to this embodiment wherein those components may function in the manner as described above and are hereby incorporated into this alternative embodiment described below. Like structures and/or components may be given like reference numerals.

As illustrated in FIG. 17, a body lumen filter 1500' can be provided with primary struts 1510' and one or more concentric secondary struts 1550'. In the illustrated example, the primary struts 1510' form the rounded portion 1570' about the perimeter of the body lumen filter 1500'. The inclusion and position of the one or more concentric secondary struts 1550' relative to the primary struts 1510' can vary the flexibility and expandability of the body lumen filter 1700. For instance, without those concentric secondary struts 1550' illustrated in dotted lines, the body lumen filter 1500' can elongate in the proximal and/or distal directions to a greater degree during packaging before and delivery. In another configuration, the body lumen filter 1500' can include concentric secondary struts 1550' within a distal portion and a portion of an intermediate portion of the body lumen filter 1500', while the proximal portion and optionally a portion of the intermediate portion are devoid of the concentric secondary struts 1550'. It will be understood that various other configurations and positions of the concentric secondary struts 1550' are possible. For instance, and not by way of limitations, although the concentric secondary struts 1550' are illustrated as being generally elongate, straight members, it will be understood that such concentric secondary struts 1550' can be curved, have a serpentine configuration, or various other configurations to aid with flexibility and expandability of the body lumen filter.

Figure 18:
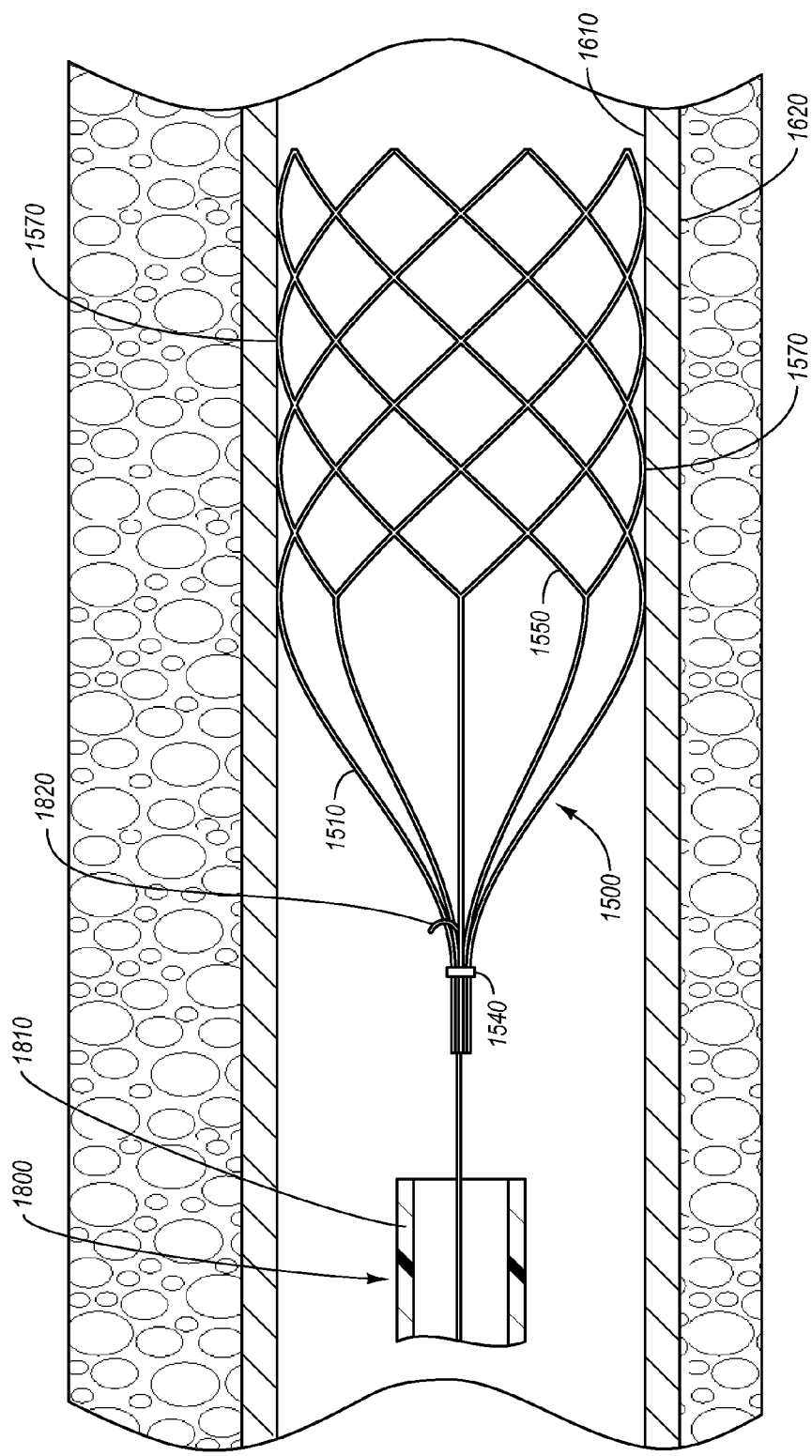
FIG. 18 illustrates a body lumen filter in a deployed state according to another example.

At some point, it may be desirable to retrieve the body lumen filter 1500. FIG. 18 illustrates a step for retrieving the body lumen filter 1500 with a retrieval device 1800. The retrieval device 1800 can include an outer housing 1810 and a retrieval feature 1820 positioned within the outer housing 1810. As illustrated in FIG. 18, retrieving the body lumen filter 1500 can include positioning the retrieval device 1800 such that the outer housing 1810 is positioned in proximity to the body lumen filter 1500. Thereafter, the retrieval feature 1820 can be moved into engagement with part of the body lumen filter 1500, such as the primary struts 1510, the ring 1540, and/or the secondary struts 1550. Thereafter, the retrieval feature 1820 can be drawn proximally relative to the outer housing 1810 to thereby draw the body lumen filter 1500 into the outer housing 1810. Once the body lumen filter 1500 is located within the retrieval device 1800, the deployment device 1800 can be removed to thereby complete retrieval of the body lumen filter 1500.

In addition, the implantable lumen filter 1700 may include one or more elements or components of the implantable lumen filters 1900, 2000 illustrated in FIGS. 19-20 and described in more detail below.

Figure 19:
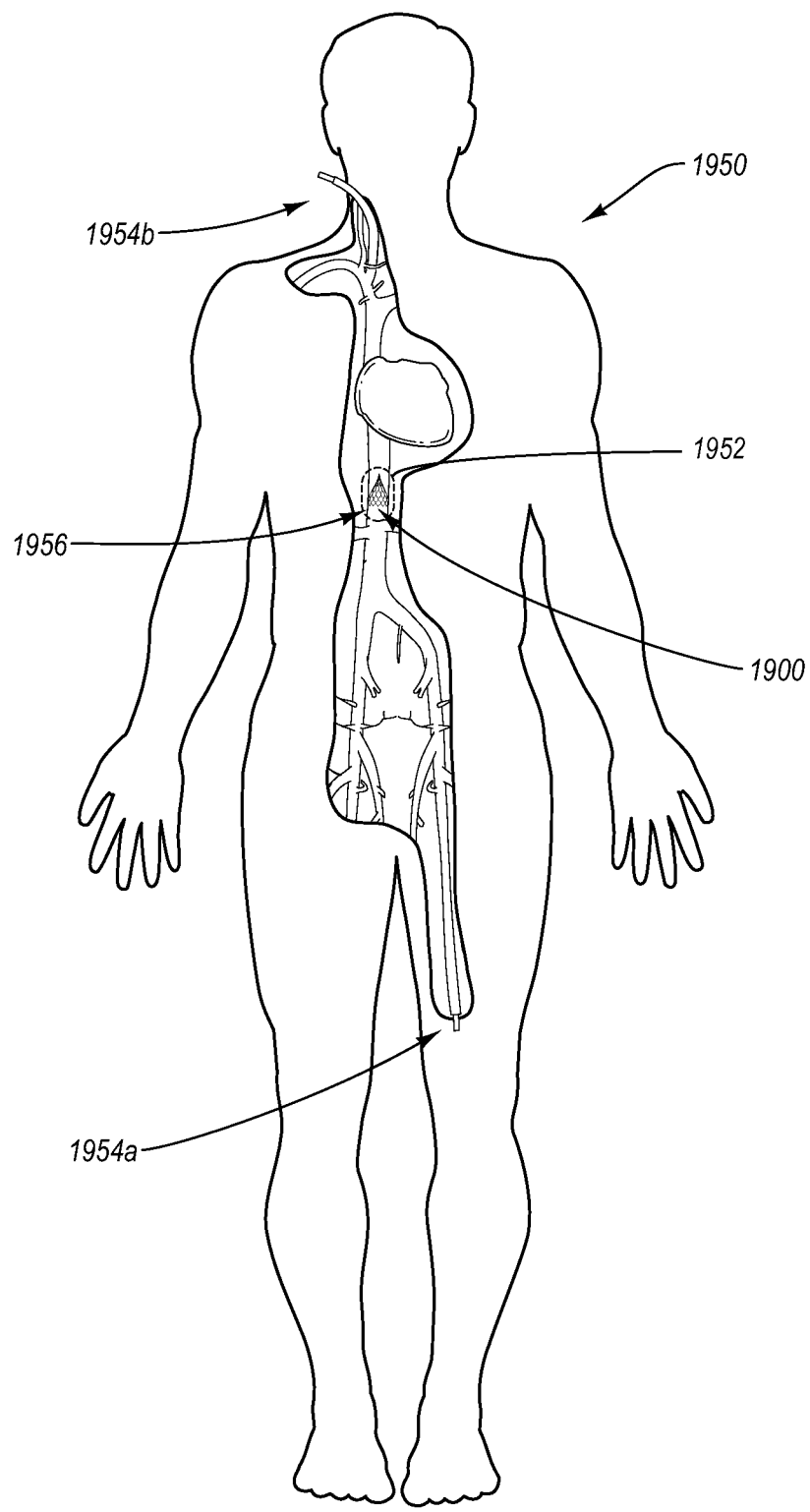
FIG. 19 illustrates an example subject for an implantable lumen filter.

FIG. 19 illustrates an exemplary subject 1950 for an implantable lumen filter 1900. The implantable lumen filter 1900 may be functionally similar to the implantable lumen filters 100, 200, 300, 400, 500, 600, 700, 800, 1100, 1200, 1300, 1400, 1500, 1700 previously described above and shown in FIGS. 1-9 and 11-18 in most respects, wherein certain features will not be described in relation to this embodiment wherein those components may function in the manner as described above and are hereby incorporated into the embodiment described below. Like structures and/or components may be given like reference numerals.

The implantable lumen filter 1900 may be implanted in a body lumen 1952 of the subject 1950. The implantable lumen filter 1900 may be inserted and/or retrieved through an access site 1954a, 1954b. In the present embodiment, the access site may include a femoral artery access site 1954a, a jugular vein access site 1954b, the radial vein, femoral vein, brachial vein, brachial artery, other access sites, or combinations of the same. For instance, the implantable lumen filter 1900 may be inserted through the femoral artery access site 1954a and retrieved through the jugular vein access site 1954b. In another example, the implantable lumen filter 1900 may be inserted through the jugular vein access site 1954b and retrieved through the femoral artery access site 1954a. The implantable lumen filter 1900 may be inserted and retrieved through the jugular vein access site 1954b. Alternatively, the implantable lumen filter 1900 may be inserted and retrieved through the femoral artery access site 1954a.

The implantable lumen filter 1900 may be deployed near a deployment site 1956. In the present embodiment, the deployment site 1956 may include a location within the interior vena cava. In other embodiments, other deployment sites may be used, such as the superior vena cava. For example, the deployment site 1956 may include all larger veins.

In addition, the implantable lumen filter 100 may include one or more elements of the implantable lumen filters 200, 300, 400, 500, 600, 700, 800, 1100, 1200, 1300, 1400, 1500, 1500 ', 1700, 1900, 2000 illustrated in FIGS. 2-8 and 11-20 and described in more detail below. In further embodiments, the implantable lumen filter 100 may include the engagement portions 920 and/or retrieval portion 1030 illustrated respectively in FIGS. 9-10 and described in more detail below.

FIGS. 20A-20G illustrate various steps in the deployment of an implantable lumen filter 2000. The implantable lumen filter 2000 may be functionally similar to the implantable lumen filters 100, 200, 300, 400, 500, 600, 700, 800, 1100, 1200, 1300, 1400, 1500, 1500', 1700, 1900 previously described above and shown in FIGS. 1-9 and 11-19 in most respects, wherein certain features will not be described in relation to this embodiment wherein those components may function in the manner as described above and are hereby incorporated into the embodiment described below. Like structures and/or components may be given like reference numerals.

Figure 20A:
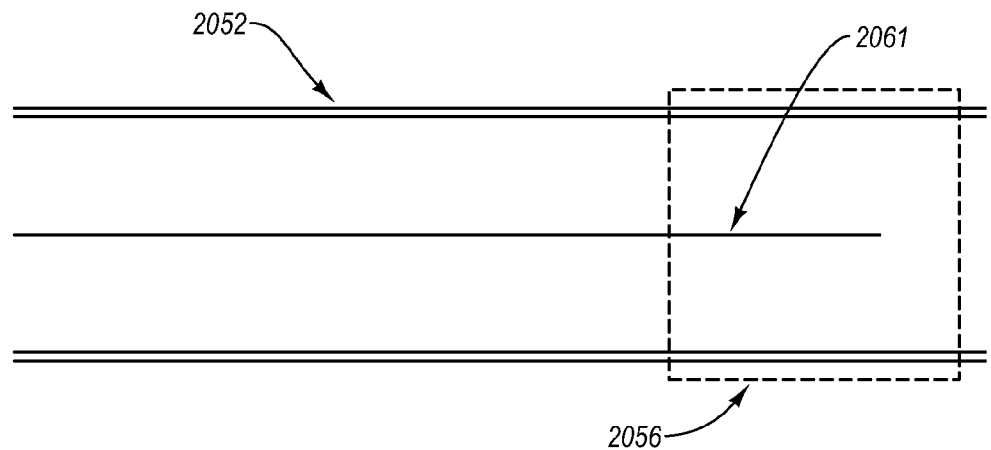
FIGS. 20A-20G' illustrate various steps in the deployment of an implantable lumen filter.

FIG. 20A illustrates a deployment site 2056 within a body lumen 2052 with a guidewire 2061 partially inserted therethrough. The guidewire 2061 may be inserted through an access site (shown as 1954a, 1954b in FIG. 19) toward the deployment site 2056. The guidewire 2061 may be used to locate the deployment site 2056. In other embodiments, other methods may be used in addition to or instead of a guidewire 2061. For example, an imaging device, such as a fluoroscope, x-ray, and/or other imaging device may be used to locate the deployment site 2056.

Figure 20B:
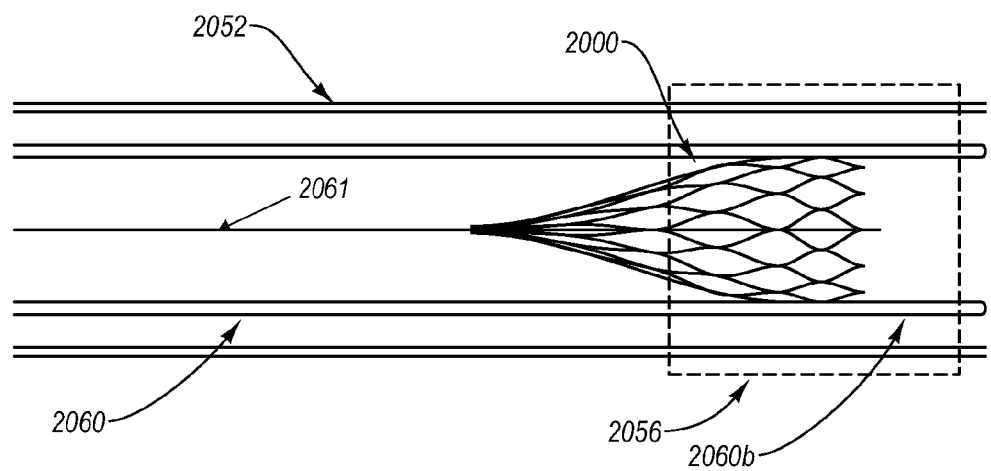

As shown in FIG. 20B, a delivery apparatus 2060 may use the guidewire 2061 to guide a distal end 2060b of the delivery apparatus 2060 toward the delivery site 2056. An implantable lumen filter 2000 may be disposed within the delivery apparatus 2060. The implantable lumen filter 2000, in the present embodiment, may be disposed within the delivery apparatus 2060 while in a collapsed state. While in the collapsed state, the implantable lumen filter 2000 may be longitudinally elongated with respect to a deployed state.

The implantable lumen filter 2000 schematically shown in FIGS. 20A-20E is similar to the implantable lumen filter 100 shown in FIG. 1. However, any component of or any of the implantable lumen filters 100, 200, 300, 400, 500, 600, 700, 800, 1100, 1200, 1300, 1400, 1500, 1500 ', 1700, 1900 shown in FIGS. 1-9 and 11-19 may be used.

The guidewire 2061 may be removed after the distal end 2060b of the delivery apparatus 2060 is located near the delivery site 2056. Alternatively, the guidewire 2061 may remain.

Figure 20C:
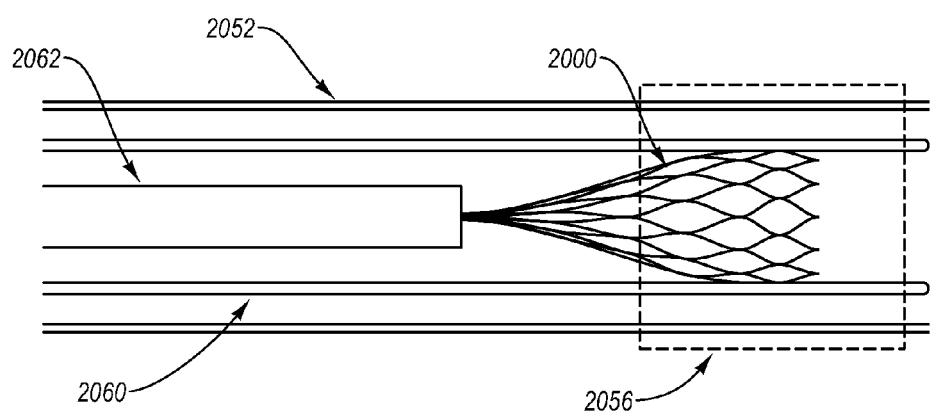

A deployment member 2062 may be inserted through the delivery apparatus 2060, as shown in FIG. 20C. The deployment member 2062 may be used to deploy the implantable lumen filter 2000. In the embodiment shown in FIG. 20D, the deployment member 2062 may urge the implantable lumen filter 2000 toward the distal end 2060b of the delivery apparatus 2060 while the delivery apparatus 2060 may remain generally stationary.

The deployment member 2062 may urge the implantable lumen filter 2000 by abutting the proximal end 2002a of the filter 2000. The deployment member 2062 may include a receiving area (not shown), such as a convex portion configured and dimensioned to receive the proximal end 2002a, to facilitate urging the implantable lumen filter 2000 out of the delivery apparatus 2060.

Figure 20D:
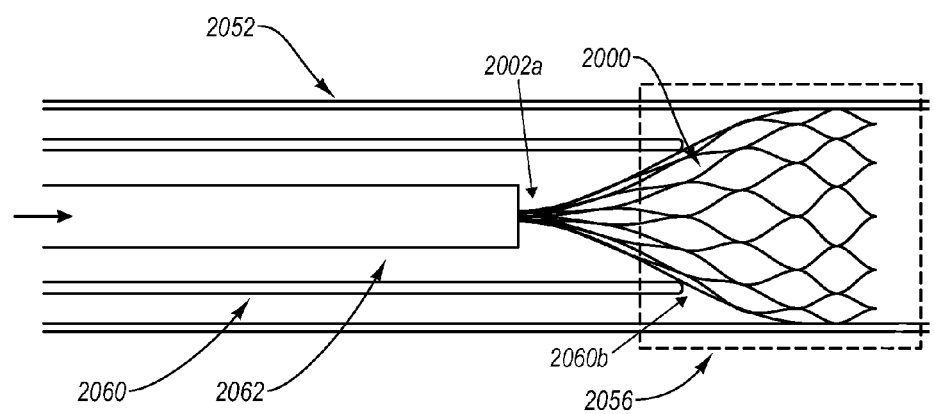
Figure 20D:
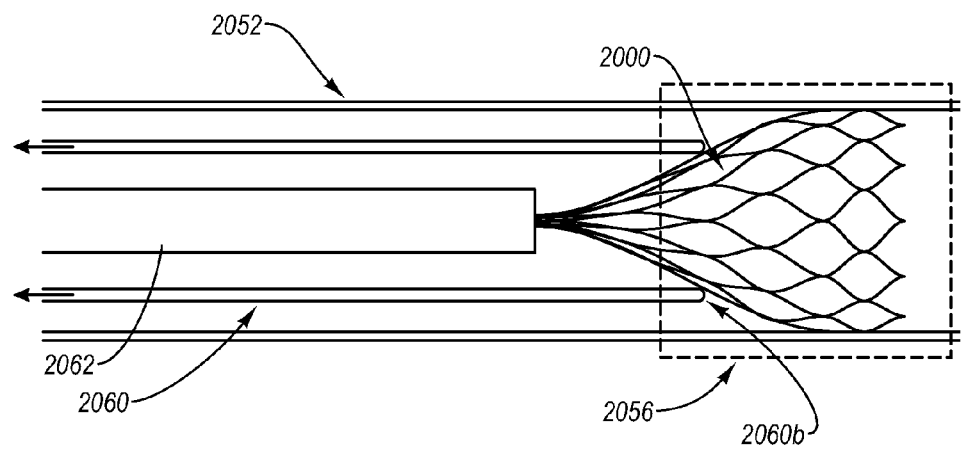

In the embodiment shown in FIG. 20D', the delivery apparatus 2060 may be retracted while the deployment member 2062 may remain generally stationary. In other embodiments, the delivery apparatus 2060 and/or the deployment member 2062 may cooperate to facilitate deployment of the implantable lumen filter 2000. For instance, the delivery apparatus 2060 may be retracted while the deployment member 2062 may urge the implantable lumen filter 2000 toward the distal end 2060b of the delivery apparatus 2060.

Figure 20E:
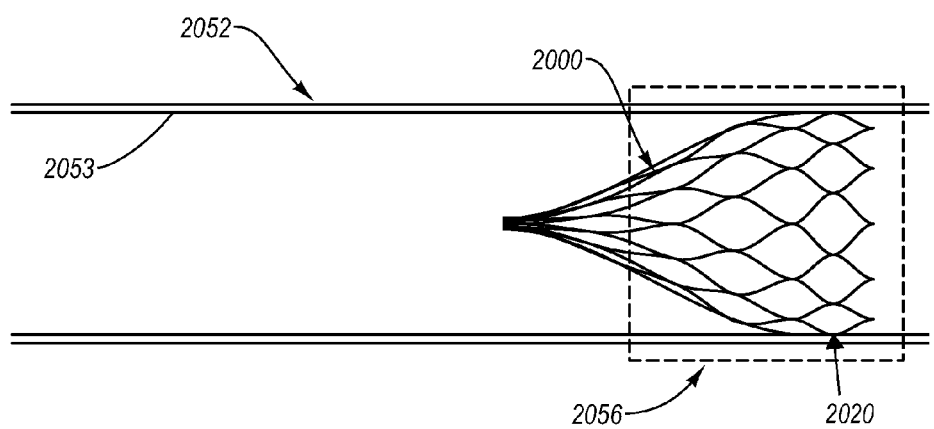

FIG. 20E illustrates a deployed implantable lumen filter 2000 within the body lumen 2052. In the deployed configuration, the implantable filter 2000 may engage an inside surface 2053 of the body lumen 2052. The engaging portion 2020 of the implantable lumen filter may engage the inside surface 2053 of the body lumen 2052. In the deployed configuration, the implantable lumen filter 2000 may be longitudinally reduced with respect to a collapsed configuration.

Figure 20F:
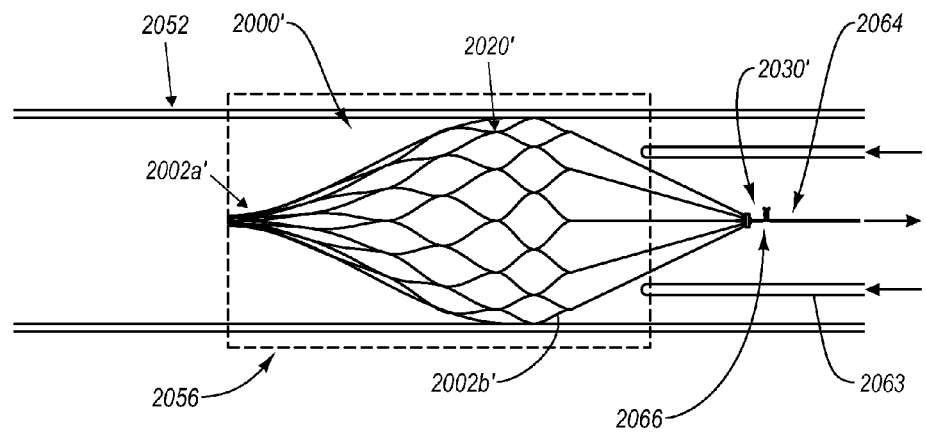
Figure 20F:
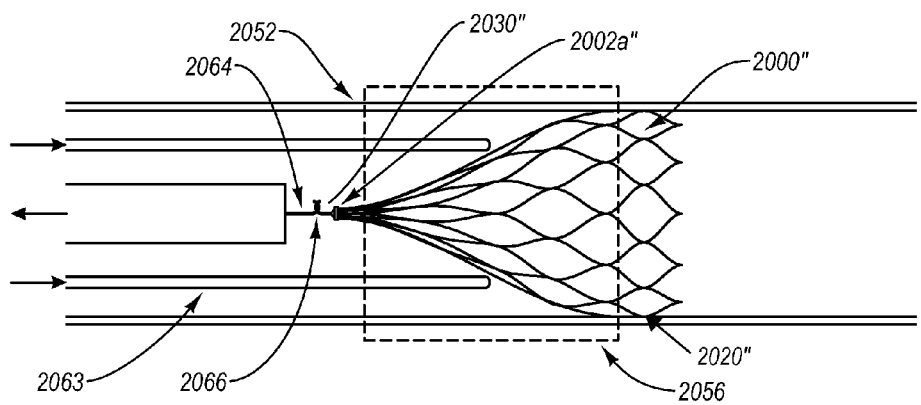
Figure 20G:
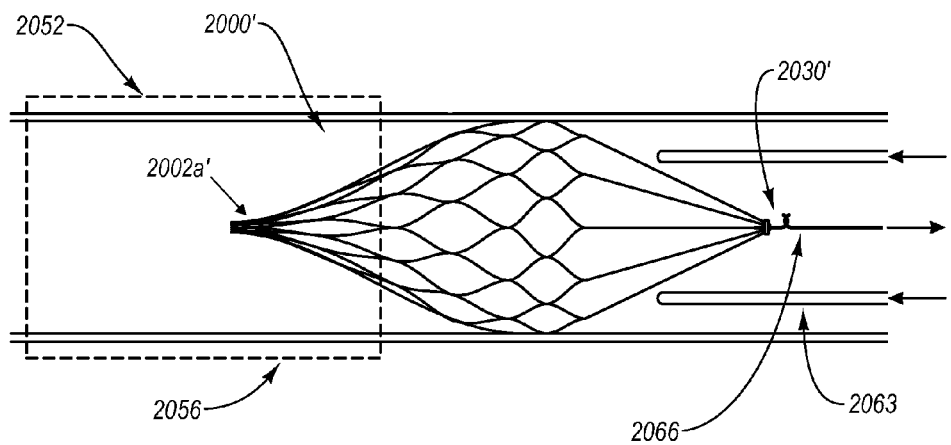
Figure 20G:
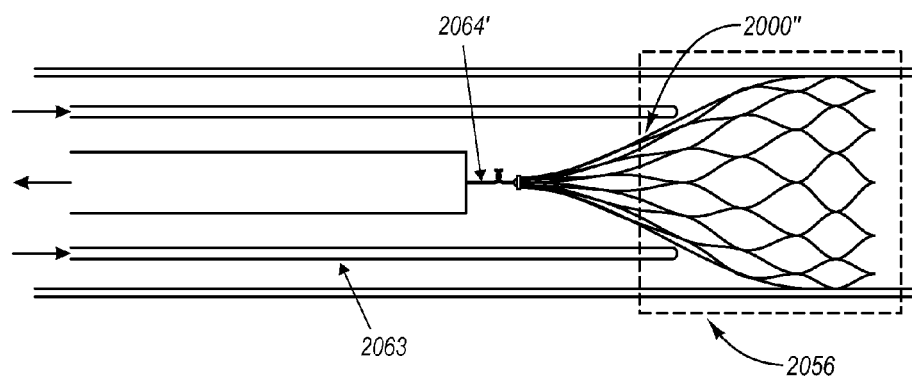

The implantable lumen filter 2000' shown in FIGS. 20E-20G may include a retrieval portion 2030' near the distal end 2020b' of the engagement portion (shown, for example, as 120 in FIG. 1) implantable lumen filter 2000'. The retrieval portion 2030' may be operatively connected to the proximal end 2002a of the implantable lumen filter 2000.

The implantable lumen filter 2000' may be engaged by a retrieval member 2064. The retrieval member 2064 may include a retrieving mechanism 2066, such as a hook and/or other retaining mechanism, configured to engage the retrieval portion 2030'.

Upon engaging the retrieval portion 2030', the retrieval member 2064 may urge the implantable lumen filter 2000' into the retrieval apparatus 2063. For example, urging the implantable lumen filter 2000' toward the retrieval apparatus 2063 may facilitate disengaging the engagement portion 2020'.

In the present embodiment, the retrieval apparatus 2063 and the retrieval member 2064 may both move in generally opposite directions to urge the implantable lumen filter 2000' into the retrieval apparatus 2063 into a compressed state, such that the implantable lumen filter 2000' may be longitudinally elongated with respect to a deployed state, as shown in FIG. 20G.

The implantable lumen filter 2000" shown in FIGS. 20F'-20G' is shown with a retrieval portion 2030' near the proximal end 2002a" of the implantable lumen filter 2000".

The implantable lumen filters 2000" may be engaged by a retrieval member 2064. The retrieval member 2064 may include a retrieving mechanism 2066, such as a hook and/or other retaining mechanism, configured to engage the retrieval portion 2030".

Upon engaging the retrieval portion 2030", the retrieval member 2064 may limit motion away from the retrieval member 2064. In the present embodiment, the retrieval member 2064 may remain generally stationary while the retrieval apparatus 2063 is advanced distally to urge the implantable lumen filter 2000" into the retrieval apparatus 2063. For example, advancing the retrieval apparatus 2063 distally may facilitate disengaging the engagement portion 2020".

In the present configuration, the retrieval member 2064 remains generally stationary while the retrieval apparatus 2063 moves to urge the implantable lumen filter 2000" into the retrieval apparatus 2063 into a compressed state, such that the implantable lumen filter 2000" may be longitudinally elongated with respect to a deployed state, as shown in FIG. 20G'. In other embodiments, both the retrieval apparatus 2063 and the retrieval member 2064 may move in generally opposite directions.

After the implantable devices 2000, 2000', 2000" are within the retrieval apparatus 2063, the retrieval apparatus 2063 and implantable devices 2000, 2000', 2000" may be withdrawn through an access site (shown as 1954a, 1954b in FIG. 19).

The embodiments described herein are susceptible to various modifications and alternative means, and specific examples thereof have been shown by way of example in the drawings and are herein described in detail. It should be understood, however, that the disclosure is not to be limited to the particular devices or methods disclosed, but to the contrary, the disclosure is to cover all modifications, equivalents, and alternatives falling within the spirit and scope of the claims.

We claim:

1. An implantable lumen filter, comprising:
a monolithic filter structure comprising:
a body portion having a proximal end, a distal end, and a generally tapered outer surface, said outer surface being formed by a plurality of struts, a plurality of the plurality of struts extending from the proximal end toward the distal end, with the plurality of struts tapering towards each other and having adjacently positioned struts disengaged, other struts of said plurality of struts forming a plurality of chevron shaped apertures, a plurality of said plurality of chevron shaped apertures being longitudinally aligned from said distal end towards said proximal end, said chevron shaped apertures being of differing areas from said distal end towards said proximal end and being dimensioned to inhibit and/or to lyse particulates of a selected size from passing through said apertures and being dimensioned to allow blood components smaller than the selected size to pass through said apertures, said body portion being transitionable from a collapsed state toward a deployed state, said distal end having a first outer dimension; and
an engaging portion having a proximal end and a distal end, said proximal end having a first outer dimension, said proximal end being operatively connected to a distal end of said body portion, said engaging portion having a generally annular shape, said engaging portion being configured to engage an inner surface of a body lumen.

2. The implantable lumen filter of claim 1, said engaging portion including a plurality of struts forming a generally diamond shaped apertures, said proximal end of said engaging portion being connected to said distal end of said body portion by connecting at least one longitudinally extending strut of said engaging portion with at least one strut of said body portion.

3. The implantable lumen filter of claim 1, said engaging portion further comprising a plurality of struts, at least a portion of said plurality of struts of said engaging portion forming a plurality of generally diamond shaped apertures, said proximal end of said engaging portion being connected to said distal end of said body portion by connecting at least one strut of said engaging portion near an apex of one said generally diamond shaped apertures of said engaging portion with at least one longitudinally extending strut of said body.

4. The implantable lumen filter of claim 3, said plurality of struts of said engaging portion having a plurality of struts connecting at least two longitudinally extending struts.

5. The implantable lumen filter of claim 4, said engaging portion further comprising a distal portion of said apertures, said distal portion being generally aligned about a longitudinal axis of said engaging portion.

6. The implantable lumen filter of claim 5, said engaging portion further comprising a proximal portion of said apertures, said proximal portion being generally aligned about the longitudinal axis of said engaging portion.

7. The implantable lumen filter of claim 6, said engaging portion further comprising at least one intermediate portion of said apertures, said at least one intermediate portion being generally aligned about the longitudinal axis of said engaging portion.

8. The implantable lumen filter of claim 1, wherein said first outer dimension of said body portion is about the same size as said first outer dimension of said engaging portion.

9. The implantable lumen filter of claim 1, said body portion having a first longitudinal dimension generally parallel with a longitudinal axis of said body portion, said engaging portion having a first longitudinal dimension generally parallel with a longitudinal axis of said engaging portion, said first longitudinal dimension of said body portion being about two thirds larger than said first longitudinal dimension of said engaging portion.

10. The implantable lumen filter of claim 1, at least a portion of said engaging portion and said struts of said body portion including cobalt chromium and/or alloys thereof or Nitinol and/or alloys thereof.

11. The implantable lumen filter of claim 1, at least a portion of said engaging portion and said body portion being coated with a thrombo-resistant, anti-proliferative, and/or anti-inflammatory coating.

12. The implantable lumen filter of claim 1, at least a portion of the material of said engaging portion and said body portion having a thrombo-resistant, anti-proliferative, and/or anti-inflammatory component incorporated therein.

13. An implantable lumen filter, comprising:
a monolithic body portion having a plurality of struts and a generally tapered shape with a tapered end, the plurality of struts including a plurality of first struts extending from the tapered end and a plurality of second struts extending between adjacently positioned first struts, each of the first struts being each disengaged from an adjacently positioned first struts and being mounted to a portion of a retrieval portion having a connecting portion and an expanded portion at least partially extending through the connecting portion, each of the plurality of second struts curving away from one of the plurality of first struts from the tapered end, the combination of the first plurality of struts and the second plurality of struts forming a plurality of chevron shaped apertures being longitudinally aligned away from said tapered end said chevron shaped apertures being dimensioned to inhibit and/or lyse particulates of a selected size from passing through said apertures and being dimensioned to allow blood components smaller than the selected size to pass through said chevron shaped apertures, said body portion being transitionable from a collapsed state toward a deployed state; and
a monolithic engaging portion having a generally annular shape and a plurality of struts, at least a portion of said plurality of struts of said engaging portion forming a plurality of generally diamond shaped apertures with generally ogee shaped proximal end and a distal end in the deployed state, said engaging portion being connected to said body portion by connecting at least one strut of said engaging portion near an apex of one of said generally diamond shaped apertures of said engaging portion with at least one strut of said body portion near an apex of one of said generally diamond shaped apertures of said body portion, said engaging portion being configured to engage an inner surface of a body lumen.

14. The implantable lumen filter of claim 13, further comprising a proximal portion of said apertures of said engaging portion, said proximal portion being generally aligned about a longitudinal axis of said engaging portion.

15. The implantable lumen filter of claim 14, further comprising a distal portion of said apertures of said engaging portion, said distal portion being generally aligned about a longitudinal axis of said engaging portion.

16. The implantable lumen filter of claim 15, further comprising at least one intermediate portion of said apertures of said engaging portion, said at least one intermediate portion being generally aligned about a longitudinal axis of said engaging portion.

17. An implantable lumen filter, comprising:
a body including a proximal end, a distal end, and a plurality of struts, said body having a generally tapered shape, said plurality of struts having a plurality of struts extending generally parallel to a longitudinal axis of said body and a plurality of struts connecting at least two longitudinally extending struts, said plurality of struts forming a plurality of apertures, said apertures being dimensioned to inhibit and/or lyse particulates of a selected size from passing through said apertures and being dimensioned to allow blood components smaller than the selected size to pass through said apertures, said body being transitionable from a collapsed state toward a deployed state, said distal end having a first outer dimension;
an engaging portion having a proximal end, a distal end, a generally annular shape, and a plurality of struts having a plurality of struts extending generally parallel to a longitudinal axis of said engaging portion and a plurality of struts connecting at least two longitudinally extending struts, said proximal end having a first outer dimension, said proximal end of said engaging portion being connected to said distal end of said body by connecting at least one longitudinally extending strut of said engaging portion with at least one longitudinally extending strut of said body, said engaging portion being configured to engage an inner surface of a body lumen; and
a plurality of tissue engaging portions connected to the plurality of struts of the engaging portion, each tissue engaging portion comprising an annular body with a tissue piercing portion extending through an annular opening of the annular body, the annular body being curved in a direction opposite to a direction in which the tissue piercing portion extends through the annular opening, with the tissue piercing portion including a bend, between a base portion of the tissue piercing portion and a piercing portion of the tissue piercing portion, remote from a junction between the annular body and the base portion.

18. The implantable lumen filter of claim 17, further comprising a proximal portion of said apertures of said engaging portion, said proximal portion being generally aligned about the longitudinal axis of said engaging portion.

19. The implantable lumen filter of claim 18, further comprising a distal portion of said apertures of said engaging portion, said distal portion being generally aligned about the longitudinal axis of said engaging portion.

20. The implantable lumen filter of claim 19, further comprising at least one intermediate portion of said apertures of said engaging portion, said at least one intermediate portion being generally aligned about the longitudinal axis of said engaging portion.

* * * * *